United States Patent [19]

Gautvik et al.

[11] Patent Number: 5,420,242

[45] Date of Patent: * May 30, 1995

[54] PRODUCTION OF HUMAN PARATHYROID HORMONE FROM MICROORGANISMS

[75] Inventors: Kaare M. Gautvik, Skovvn 17, Oslo, Norway, 0257 2; Peter Alestrom, Sakseveien 24, Sollihogda, Norway, 3505; Tordis B. Oyen, Oslo, Norway

[73] Assignees: Kaare M. Gautvik; Peter Alestrom, both of Norway

[ * ] Notice: The portion of the term of this patent subsequent to Apr. 23, 2008 has been disclaimed.

[21] Appl. No.: 87,471

[22] Filed: Jul. 2, 1993

Related U.S. Application Data

[63] Continuation of Ser. No. 821,478, Jan. 15, 1992, abandoned, which is a continuation of Ser. No. 404,970, Sep. 8, 1989, abandoned, which is a continuation-in-part of Ser. No. 393,851, Aug. 14, 1989, Pat. No. 5,010,010, which is a continuation of Ser. No. 921,684, Oct. 22, 1986, abandoned.

[51] Int. Cl.[6] .......................... C07K 7/36; C12N 15/16
[52] U.S. Cl. .................... 530/307; 536/23.51
[58] Field of Search .................... 435/320.1, 69.1; 530/307; 536/23.51

[56] References Cited

U.S. PATENT DOCUMENTS

| | | | |
|---|---|---|---|
| 4,237,224 | 12/1980 | Cohen et al. | 435/172.3 |
| 4,264,731 | 4/1981 | Shine | 435/172.3 |
| 4,338,397 | 7/1982 | Gilbert et al. | 435/69.1 |
| 4,366,246 | 12/1982 | Riggs | 435/69.1 |
| 4,394,443 | 7/1983 | Weissman et al. | 435/69.1 |
| 4,425,437 | 1/1984 | Riggs | 435/69.1 |
| 4,468,464 | 8/1984 | Cohen et al. | 435/172.3 |
| 4,532,207 | 7/1985 | Brewer et al. | 435/69.1 |
| 4,546,082 | 10/1985 | Kurjan et al. | 435/69.1 |
| 4,588,684 | 5/1986 | Brake | 435/69.1 |
| 4,904,584 | 2/1990 | Shaw | 435/69.4 |
| 5,010,010 | 4/1991 | Gautvik et al. | 435/252.3 |

FOREIGN PATENT DOCUMENTS

| | | | |
|---|---|---|---|
| 038183 | 10/1981 | European Pat. Off. | 435/69.1 |
| 123544 | 10/1984 | European Pat. Off. | |
| 139076 | 5/1985 | European Pat. Off. | 435/69.1 |
| 2092596 | 8/1982 | United Kingdom | 435/69.1 |
| 2094833 | 9/1982 | United Kingdom | 435/69.1 |
| 8401173 | 3/1984 | WIPO | 435/69.1 |

OTHER PUBLICATIONS

Kronenberg et al., "Studies of Parathyroid Hormone Secretion Using Recombinant DNA Technology," *Endocrine Control of Bone and Calcium Metabolism*, 217 (1984).

Born et al., (Abstract) "Expression of Human Preproparathyroid Hormone in *E. coli* and Yeast," *Calcified Tissue International*, vol. 35, 679 (1983).

Born et al., (Abstract) "Expression of Human Preproparathyroid Hormone in *E. coli* and Yeast," *Calcified Tissue International*, vol. 36 (Suppl. 2), 287 (1984).

Hendy et al., "Nucleotide Sequence of Cloned cDNAs Encoding Human Preproparathyroid Hormone," *Proc. Natl. Acad. Sci. USA*, vol. 78, 7365 (1981).

(List continued on next page.)

*Primary Examiner*—Richard A. Schwartz
*Assistant Examiner*—James Ketter
*Attorney, Agent, or Firm*—Lerner, David, Littenberg, Krumholz & Mentlik

[57] ABSTRACT

The invention provides recombinant plasmids containing in DNA sequences coding for human preproparathyroid hormone. The invention further provides microorganisms, for example *E. coli*, transformed by these plasmids. The invention also provides a plasmid for insertion into yeast and a transformed yeast in which the plasmid contains DNA coding for parathyroid hormone. Parathyroid hormone is then secreted by the transformed yeast. Further the invention provides alternate polypeptides having parathyroid hormone activity, including PTH analogs, fragments and extensions, and provides alternate leader sequences and secretion signal sequences which can be used in the present invention. Finally, there are provided methods for purification of the secreted PTH hormone and/or derivatives.

10 Claims, 20 Drawing Sheets

OTHER PUBLICATIONS

Breyel et al., "Synthesis of Mature Human Parathyroid Hormone in *Escherichia coli*," *Third European Congress on Biotechnology*, Vo. III, 363 (1984).

Breyel et al., (Abstract) "Synthesis of Mature Human Parathyroid Hormone in *Escherichia coli*," *Calcified Tissue International*, vol. 36 (Suppl. 2), 297 (1984).

Born et al., (Abstract) "Expression And Processing of Human Preproparathyroid Hormone in *Escherichia coli*," *Experientia*, vol. 39, 659 (1983).

Hendy, (Abstract) "Cloning of Human Parathyroid Hormone mRNA and Gene," *Calcified Tissue International*, vol. 36, 286 (1984).

McDevitt et al., (Abstract) "Isolation of Human Parathyroid Hormone Genes," *Calcified Tissue International*, vol. 31, 74 (1980).

Gordon et al., (Abstract) "Molecular Cloning and Structural Analysis of Near Full-Length DNA Complementary to the mRNA Coding for Bovine Parathyroid Hormone," *Fed. Proc.*, 39, 947 (1980).

Vasicek et al., "Nucleotide Sequence of the Human Parathyroid Hormone Gene," *Proc. Nat'l. Acad. Sci.*, vol. 80, 2127 (1983).

Kronenberg et al., "Cloning and Nucleotied Sequence of DNA Coding for Bovine Preproparathyroid Hormone," *Proc. Nat'l Acad. Sci.*, vol. 76, 4981 (1979).

Sung et al., "Hybrid Gene Synthesis: Its Application to the Assembly of DNA Sequences Encoding the Human Parathyroid Hormones and Analogues," *Biochem. Cell Biol.*, vol. 64, 133 (1986).

Keutmann et al., "Complete Amino Acid Sequence of Human Parathyroid Hormone," *Biochemistry*, vol. 17, 5723 (1978).

Naylor et al., "Human Parathyroid Hormone Gene (PTH) is on Short Arm of Chromosome II," *Somatic Cell Genetics*, vol. 9 (1983).

Kronenberg et al., (Abstract) "Structural Analysis of the Human Parathyroid Hormone Gene," *Calcified Tissue International*, vol. 33, 322 (1981).

Hellerman et al., "Secretion of Human Parathyroid Hormone from Rat Pituitary Cells Infected with a Recombinant Retrovirus Encoding Preproparathyroid Hormone," *Proc. Nat'l. Acad. Sci.*, vol. 81, 5340 (1984).

Brake et al., Alpha-Factor-directed synthesis and secretion of mature foreign proteins in Saccharomyces cerevisiae, Mar. 28, 1984.

Cantrell et al., cDNA Cloning, Expression, and Activity of Human Granulocyte-Macrophage Colony-Stimulating Factor, 1987.

Arnst, J. F., Efficient Secretion and Processing of Heterologous Protein in Saccharomyces cerevisiae is mediated solely by the Pre-Segment of Alpha-Factor Precursor, DNA 7 (1988).

FIG. 1
DNA SEQUENCE FOR HUMAN PREPROPARATHYROID HORMONE

```
         10                  30                  50
ATGATHCCNGCNAARGAYATGGCNAARGTNATGATHGTNATGYTNGCNATHTGYTTYYTN 70                  90                 110
ACNAARWSNGAYGGNAARWSNGTNAARAARMGNWSNGTNWSNGARATHCARYTNATGCAY 130                 150                 170
AAYYTNGGNAARCAYYTNAAYWSNATGGARMGNGTNGARTGGYTNMGNAARAARYTNCAR 190                 210                 230
GAYGTNCAYAAYTTYGTNGCNYTNGGNGCNCCNYTNGCNCCNMGNGAYGCNGGNWSNCAR 250                 270                 290
MGNCCNMGNAARAARGARGAYAAYGTNYTNGTNGARWSNCAYGARAARWSNYTNGGNGAR 310                 330
GCNGAYAARGCNGAYGTNAAYGTNYTNACNAARGCNAARWSNCARTRR
```

DNA SEQUENCE FOR HUMAN PREPROPARATHYROID HORMONE IN PLASMID pSSHPTH-10

```
          10                  30                  50
TATGATGATACCTGCAAAAGACATGGCTAAAGTTATGATTGTCATGTTGGCAATTTGTTT 70                  90                  110
TCTTACAAAATCGGATGGGAAATCTGTTAAGAAGAGATCGTGGAGTGAAATACAGCTTAT 130                 150                 170
GCATAACCTGGGAAAACATCTGAACTCGATGGAGAGAGTAGAATGGCTGCGTAAGAAGCT 190                 210                 230
GCAGGATGTGCACAATTTTGTTGCCCTTGGAGCTCCTCTAGCTCCCAGAGATGCTGGTTC 250                 270                 290
CCAGAGGCCCCGAAAAAAGGAAGACAATGTCTTGGTTGAGAGCCATGAAAAAAGTCTTGGA 310                 330
GAGGCAGACAAAGCTGATGTGAATGTATTAACTAAAGCTAAATCCCAGTGA
```

FIG. 3

PORTION OF DNA SEQUENCE OF THE PLASMID
FOR INSERTION INTO E. COLI, CODING FOR HUMAN
PREPROPARATHYROID HORMONE WITH FLANKING SEQUENCES.

```
          10                  30                  50
TATGATGATHCCNGCNAARGAYATGGCNAARGTNATGATHGTNATGYTNGCNATHTGYTT 70                  90                  110
YYTNACNAARWSNGAYGGNAARWSNGTNAARAARMGNWSNGTNWSNGARATHCARYTNAT 130                 150                 170
GCAYAAYYTNGGNAARCAYYTNAAYWSNATGGARMGNGTNGARTGGYTNMGNAARAARYT 190                 210                 230
NCARGAYGTNCAYAAYTTYGTNGCNYTNGGNGCNCCNYTNGCNCCNMGNGAYGCNGGNWS 250                 270                 290
NCARMGNCCNMGNAARAARGARGAYAAYGTNYTNGTNGARWSNCAYGARAARWSNYTNGG 310                 330                 350
NGARGCNGAYAARGCNGAYGTNAAYGTNYTNACNAARGCNAARWSNCARTRRAAATGAAA 370                 390                 410
ACAGATATTGTCAGAGTTCTGCTCTAGACAGTGTAGGGCAACAATACATGCTGCTAATTC

430
AAAGCTCTATTA
```

DNA SEQUENCE FOR HUMAN PREPROPARATHYROID
HORMONE IN PLASMID pSSHPTH-10 WITH FLANKING SEQUENCES

```
          10                  30                  50
TATGATGATACCTGCAAAAGACATGGCTAAAGTTATGATTGTCATGTTGGCAATTTGTTT 70                  90                 110
TCTTACAAAATCGGATGGGAAATCTGTTAAGAAGAGATCTGTGAGTGAAATACAGCTTAT 130                 150                 170
GCATAACCTGGGAAAACATCTGAACTCGATGGAGAGAGTAGAATGGCTGCGTAAGAAGCT 190                 210                 230
GCAGGATGTGCACAATTTTGTTGCCCTTGGAGCTCCTCTAGCTCCCAGAGATGCTGGTTC 250                 270                 290
CCAGAGGCCCCGAAAAAAGGAAGACAATGTCTTGGTTGAGAGCCATGAAAAAAGTCTTGG 310                 330                 350
AGAGGCAGACAAAGCTGATGTGAATGTATTAACTAAAGCTAAATCCCAGTGAAAATGAAA 370                 390                 410
ACAGATATTGTCAGAGTTCTGCTCTAGACAGTGTAGGGCAACAATACATGCTGCTAATTC

430
AAAGCTCTATTA
```

FIG. 5

DNA SEQUENCE CODING FOR PREPROPARATHYROID HORMONE
IN pSSHPTH-10 WITH FLANKING SEQUENCES, SHOWING
THE CORRESPONDING AMINO ACID SEQUENCE OF
PREPROPARATHYROID HORMONE

```
        10                  30                  50
TATGATGATACCTGCAAAAGACATGGCTAAAGTTATGATTGTCATGTTGGCAATTTGTTT
    MetIleProAlaLysAspMetAlaLysValMetIleValMetLeuAlaIleCysPh 70                  90                 110
TCTTACAAAATCGGATGGGAAATCTGTTAAGAAGAGATCTGTGAGTGAAATACAGCTTAT
eLeuThrLysSerAspGlyLysSerValLysLysArgSerValSerGluIleGlnLeuMe 130                 150                 170
GCATAACCTGGGAAAACATCTGAACTCGATGGAGAGAGTAGAATGGCTGCGTAAGAAGCT
tHisAsnLeuGlyLysHisLeuAsnSerMetGluArgValGluTrpLeuArgLysLysLe 190                 210                 230
GCAGGATGTGCACAATTTTGTTGCCCTTGGAGCTCCTCTAGCTCCCAGAGATGCTGGTTC
uGlnAspValHisAsnPheValAlaLeuGlyAlaProLeuAlaProArgAspAlaGlySe 250                 270                 290
CCAGAGGCCCCGAAAAAAGGAAGACAATGTCTTGGTTGAGAGCCATGAAAAAAGTCTTGG
rGlnArgProArgLysLysGluAspAsnValLeuValGluSerHisGluLysSerLeuGl 310                 330                 350
AGAGGCAGACAAAGCTGATGTGAATGTATTAACTAAAGCTAAATCCCAGTGAAAATGAAA
yGluAlaAspLysAlaAspValAsnValLeuThrLysAlaLysSerGlnEnd 370                 390                 410
ACAGATATTGTCAGAGTTCTGCTCTAGACAGTGTAGGGCAACAATACATGCTGCTAATTC

430
AAAGCTCTATTA
```

FIG. 6

PARTIAL DNA SEQUENCE FOR THE PLASMID FOR INSERTION INTO YEAST IN WHICH: NUCLEOTIDE NOS. 1-173 MAKEUP THE MF 1 PROMOTER REGION AND 5' NONCODING SEQUENCE. 174-440 IS THE MF 1 N-TERMINAL CODING SEQUENCE. 441-695 IS AN HPTH SEQUENCE. 696-726 IS AN HPTH 3' NONCODING SEQUENCE FROM pSSHPTH-10. 727-732 IF FROM pUC19. 733-874 IS MF 1 3' NONCODING SEQUENCE AND TRANSCRIPTIONAL TERMINATION SIGNAL

```
          10                            30
AGTGCAAGAAAACCAAAAAGCAACAACAGGTTTTGGATAAGTACATATATAAGAGGGCCT
          70           90            110
TTTGTTCCCATCAAAAATGTTACTGTTCTTACGATTCATTTACGATTCAAGAATAGTTCA
          130          150           170
AACAAGAAGATTACAAACTATCAATTTCATACACAATATAAACGACCAAAAGAATGAGAT
          190          210           230
TTCCTTCAATTTTTACTGCAGTTTTATTCGCAGCATCCTCCGCATTAGCTGCTCCAGTCA
          250          270           290
ACACTACAACAGAAGATGAAACGGCACAAATTCCGGCTGAAGCTGTCATCGGTTACTCAG
          310          330           350
ATTTAGAAGGGGATTTCGATGTTGCTGTTTTGCCATTTTCCAACAGCACAAATAACGGGT
          370          390           410
TATTGTTTATAAATACTACTATTGCCAGCATTGCTGCTAAAGAAGAAGGGGTATCTTTGG
          430          450           470
ATAAAAGAGAGGCTGAAGCTWSNGTNWSNGARATHCARYTNATGCAYAAYYTNGGNAARC
          490          510           530
AYYTNAAYWSNATGGARMGNGTNGARTGGYTNMGNAARAARYTNCARGAYGTNCAYAAYT
          550          570           590
TYGTNGCNYTNGGNGCNCCNYTNGCNCCNMGNGAYGCNGGNWSNCARMGNCCNMGNAARA
          610          630           650
ARGARGAYAAYGTNYTNGTNGARWSNCAYGARAARWSNYTNGGNGARGCNGAYAARGCNG
          670          690           710
AYGTNAAYGTNYTNACNAARGCNAARWSNCARTRRAAATGAAAACAGATATTGTCAGAGT
          730          750           770
TCTGCTCTAGAGTCGACTTTGTTCCCACTGTACTTTTAGCTCGTACAAAATACAATATAC
          790          810           830
TTTTCATTTCTCCGTAAACAACCTGTTTTCCCATGTAATATCCTTTTCTATTTTTCGTTT
          850          870
CGTTACCAACTTTACACATACTTTATATAGCTAT, WHEREIN
```

NUCLEOTIDE SEQUENCE OF THE MF 1-HPTH FISION GENE FROM pS LX5-HPTH1. NUCLEOTIDE NOS. 1-173 MAKEUP THE MH 1 PROMOTER REGION AND 5' NONCODING SEQUENCE. 174-440 IS THE MF 1 N-TERMINAL CODING SEQUENCE. 441-695 IS THE HPTH SEQUENCE OBTAINED FROM pSSHPTH-10. 696-726 IS AN HPTH 3' NONCODING SEQUENCE FROM pSSHPTH-10. 727-732 IS FROM pUC19. 733-874 IS MF 1 3' NONCODING SEQUENCE AND TRANSCRIPTIONAL TERMINATION SIGNAL

```
              10                  30                  50
    AGTGCAAGAAAACCAAAAAGCAACAACAGGTTTTGGATAAGTACATATATAAGAGGGCCT
              70                  90                 110
    TTTGTTCCCATCAAAAATGTTACTGTTCTTACGATTCATTTACGATTCAAGAATAGTTCA
             130                 150                 170
    AACAAGAAGATTACAAACTATCAATTTCATACACAATATAAACGACCAAAAGAATGAGAT
             190                 210                 230
    TTCCTTCAATTTTTACTGCAGTTTTATTCGCAGCATCCTCCGCATTAGCTGCTCCAGTCA
             250                 270                 290
    ACACTACAACAGAAGATGAAACGGCACAAATTCCGGCTGAAGCTGTCATCGGTTACTCAG
             310                 330                 350
    ATTTAGAAGGGGATTTCGATGTTGCTGTTTTGCCATTTTCCAACAGCACAAATAACGGGT
             370                 390                 410
    TATTGTTTATAAATACTACTATTGCCAGCATTGCTGCTAAAGAAGAAGGGGTATCTTTGG
             430                 450                 470
    ATAAAAGAGAGGCTGAAGCTTCTGTGAGTGAAATACAGCTTATGCATAACCTGGGAAAAC
             490                 510                 530
    ATCTGAACTCGATGGAGAGAGTAGAATGGCTGCGTAAGAAGCTGCAGGATGTGCACAATT
             550                 570                 590
    TTGTTGCCCTTGGAGCTCCTCTAGCTCCCAGAGATGCTGGTTCCCAGAGGCCCCGAAAAA
             610                 630                 650
    AGGAAGACAATGTCTTGGTTGAGAGCCATGAAAAAAGTCTTGGAGAGGCAGACAAAGCTG
             670                 690                 710
    ATGTGAATGTATTAACTAAAGCTAAATCCCAGTGAAAATGAAAACAGATATTGTCAGAGT
             730                 750                 770
    TCTGCTCTAGAGTCGACTTTGTTCCCACTGTACTTTTAGCTCGTACAAAATACAATATAC
             790                 810                 830
    TTTTCATTTCTCCGTAAACAACCTGTTTTCCCATGTAATATCCTTTTCTATTTTTCGTTT
             850                 870
    CGTTACCAACTTTACACATACTTTATATAGCTAT
```

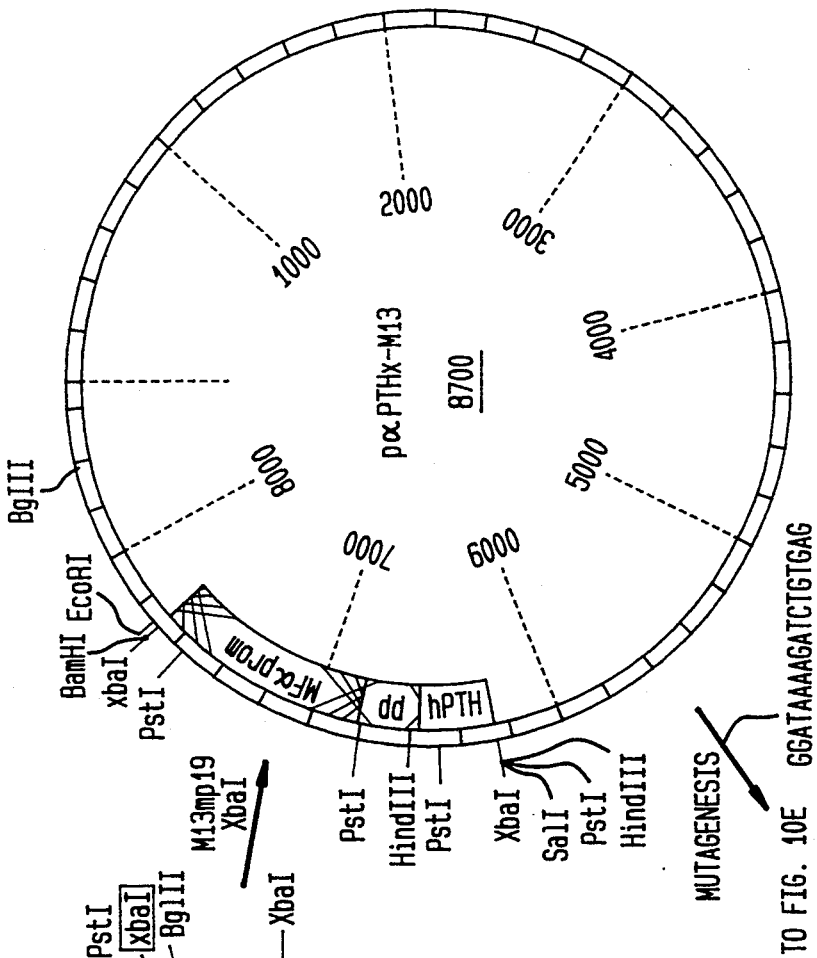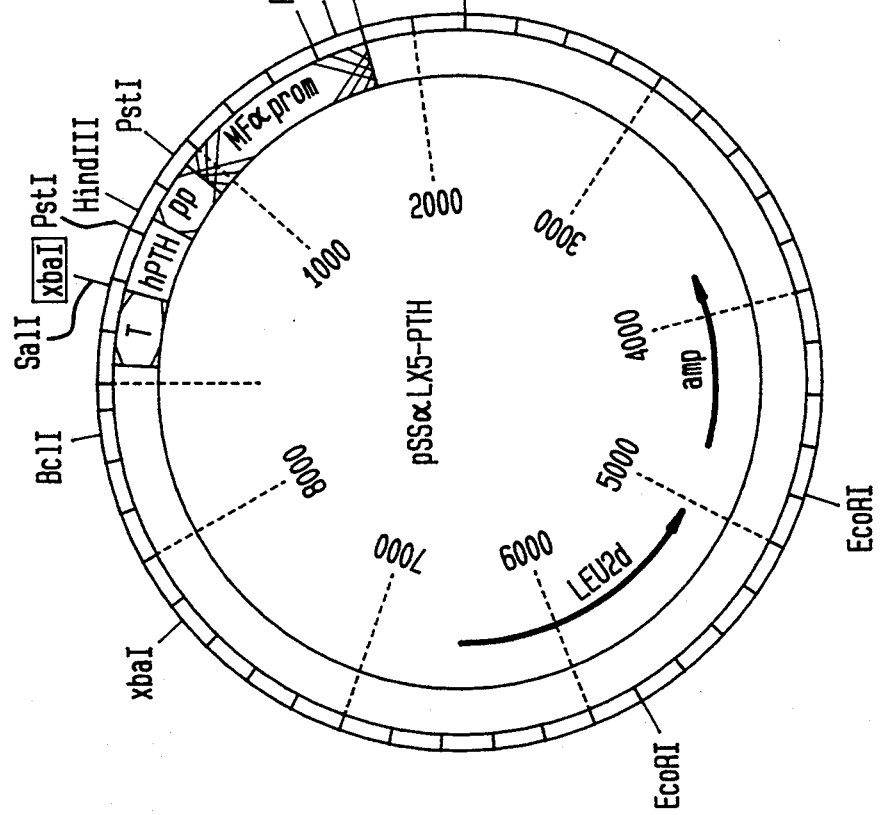

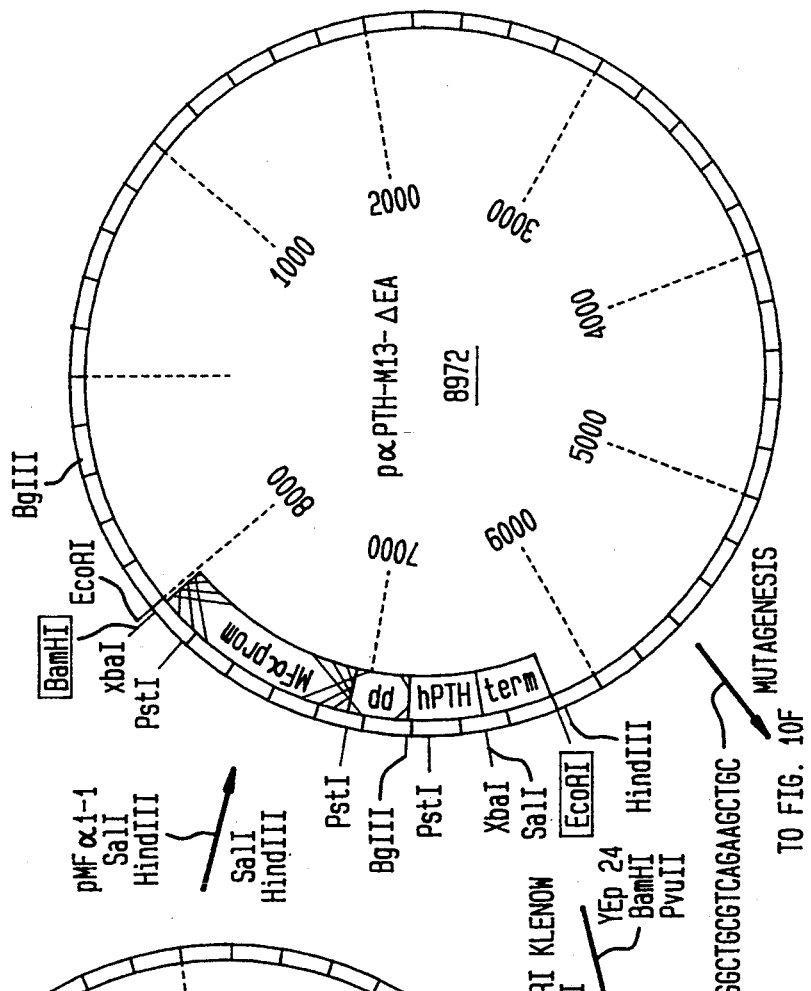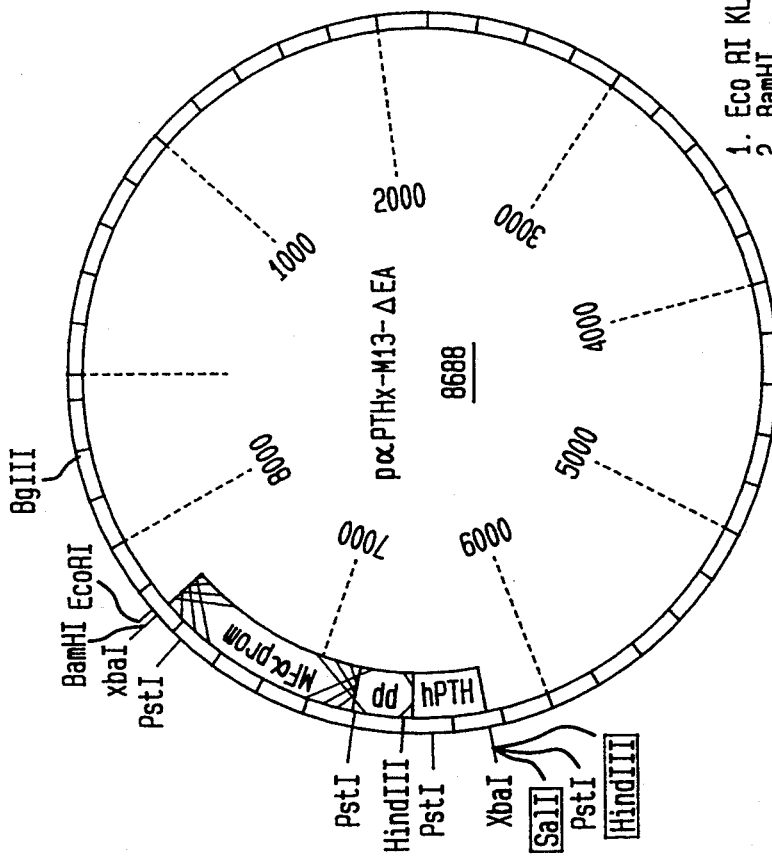
FIG. 10D
FIG. 10C

IN vitro MUTAGENESIS OF hPTH

HPLC CHROMATOGRAM OF hPTH (Q26)

PRODUCTION OF HUMAN PARATHYROID HORMONE FROM MICROORGANISMS

This is a continuation, of application Ser. No. 07/821,478 filed Jan. 15, 1992, now abandoned which is a Continuation of Ser. No. 07/404,970 filed Sep. 8, 1989, abandoned which is a CIP of Ser. No. 07/393,851 filed Aug. 14, 1989, now U.S. Pat. No. 5,010,010, which is a Continuation of Ser. No. 06/921,684 filed on Oct. 22, 19986, now abandoned.

FIELD OF THE INVENTION

This invention relates to genetically engineered microorganisms containing DNA coding for human pre-proparathyroid hormone.

BACKGROUND OF THE INVENTION

A number of proteins and peptides that are normally synthesized by mammalian cells have proven to have medical, agricultural and industrial utility. These proteins and peptides may be of different molecular size and have a number of different functions, for example, they may be enzymes, structural proteins, growth factors and hormones. In essence both proteins and peptides are composed of linear sequences of amino acids which form secondary and tertiary structures that are necessary to convey the biological activity. Human parathyroid hormone has a relatively small molecular weight, which has made it possible to synthesize the peptide chemically by the sequential addition of amino acids. Thus, parathyroid hormone is commercially available, but in very small quantities at high cost. As a result, there is no human parathyroid hormone available at a reasonable price to supply the many potential medical, agricultural and industrial applications.

During the past ten years, microbiological techniques employing recombinant DNA have made it possible to use microorganisms for the production of species-different peptides. The microorganism is capable of rapid and abundant growth and can be made to synthesize the foreign product in the same manner as bacterial peptides. The utility and potential of this molecular biological approach has already been proven by microbiological production of a number of human proteins that are now available for medical and other uses.

Parathyroid hormone (PTH) is one of the most important regulators of calcium metabolism in mammals and is also related to several diseases in humans, animals, e.g. milk fever, acute hypocalsemia and otherwise pathologically altered blood calcium levels. This hormone therefore will be important as a part of diagnostic kits and will also have potential as a therapeutic in human and veterinary medicine.

The first synthesis of DNA for human preproparathyroid hormone was described by Hendy, G. N., Kronenberg, H. M., Potts, Jr. J. T. and Rich, A. 78 Proc. Natl. Acad. Sci. 7365–7369 (1981). DNA complementary in sequence to PTH mRNA was synthesized and made double stranded (Hendy et al. supra). This cDNA was cloned in pBR 322 DNA and E. coli X1776 was transfected. Of the colonies with correct antibiotic resistance, 23 out of 200 clones were identified as containing specific human PTH cDNA inserts. However, none of the 23 human PTH clones contained the full length insert (Hendy et al., supra). Later Breyel, E., Morelle, G., Auf'mkolk, B., Frank, R., Blocker, H. and Mayer, H., Third European Congress on Biotechnology, 10–14 Sep. 1988, Vol. 3, 363–369 described the presence of the human PTH gel in a fetal liver genomic DNA library constructed in the phage Charon 4A. A restriction enzyme fragment of the PTH gene was recloned and transfected into E. coli.

However, the work of Breyel, supra, demonstrate that E. coli degrades human PTH. Thus, a microorganism which shows a stable production of intact human parathyroid hormone has so far not been described. Further, parethyroid hormone has never before been isolated from yeast.

SUMMARY OF THE INVENTION

Accordingly, it is an object of the preset invention to provide a plasmid containing DNA coding for human preproparathyroid hormone (HPTH) for insertion in Escherichia coli. It is another object of the present invention to provide a genetically engineered E. coli containing DNA coding for human preproparathyroid hormone.

A further object of the present invention is to provide a plasmid for insertion in yeast containing DNA coding for parathyroid hormone ("PTH"), It is also an object of the present invention to provide a transformed yeast containing DNA coding for parathyroid hormone including human parathyroid hormone, and from which transformed yeast, parathyroid hormone may be obtained.

Another object of the present invention is to provide new polymers having parathyroid hormone activity including PTH fragments, extension and analogs. Yet another object is to provide alternate leader sequences and secretion signal sequences which can be used in the practice of the present invention.

A still further object of the invention is to provide downstream process technology for purification of intact PTH, as well as purification of analogs, fragments and extensions.

Other objects and advantages of the present invention will become apparent as the description thereof proceeds.

In satisfaction of the foregoing objects and advantages, there is provided by the present invention a novel plasmid for insertion in E. coli, containing DNA coding for human preproparathyroid hormone. The plasmid when inserted into E. coli functions to transform the E. coli such that the E. coli then produces multiple copies of the plasmid and thus of the CDNA coding for human preproparathyroid hormone. The plasmid for human insertion into E. Coli of the present invention and thus the transformed E. coli are distinguishable over prior art plasmids and microorganisms, for example as described in Hendy et al., supra, in that the plasmid of the present invention contains a double start codon at the 5' end of the DNA coding for preproparathyroid hormone. The presence of the double start codon may cause a production microorganisms transformed with a plasmid containing the cDNA to produce preproparathyroid hormone at an increased rate and in an improved yield over prior art transformed microorganisms.

There is further provided by the present invention a plasmid for insertion into yeast containing DNA coding for parathyroid hormone. In a preferred embodiment, this plasmid is prepared by recloning the plasmid for insertion in E. coli described above. Moreover, the invention provides a yeast transformed by said plasmid for insertion in yeast such that the yeast produces and secretes parathyroid hormone. Thus, the invention provides a method by which parathyroid hormone may be isolated from yeast culture medium. In a preferred embodiment, the transformed yeast is *Saccharomyces cerevisiae*. In another preferred embodiment, the parathyroid hormone is human parathyroid hormone.

By use of in vitro mutagenesis, the present invention also provides substitution of one or more amino acids in human parathyroid hormone and peptides having parathyroid hormone agonistic or antagonistic activity. Further, there is provided analogs, fragments, or extensions of the parathyroid hormone (collectively referred to as "derivatives") which also show agonistic or antagonistic activity. Examples of these peptides have been produced as secretory products in yeast and in *E. coli*.

The present invention further provides different leader sequences and secretion signal sequences that may be used for the production and secretion of the PTH hormone and/or its derivatives. In at least one instance, an alternate leader sequence provides improved production of the desired hormone or derivative.

Additionally, the invention provides a downstream process technology for purification of human parathyroid hormone and derivatives. The process involves a purification procedure for yeast or *E. coli* medium or periplasmic solution, and consists principally of cation exchange chromatography followed by two steps of high pressure liquid chromatography. The final product is more than 95 percent pure and can be submitted directly to N-terminal amino acid sequencing as well as amino acid composition determination.

Human parathyroid hormone (hPTH) is a key regulator of calcium homeostasis. The hormone is produced as a 115 amino-acid prepro-peptide. Before secretion the prepro part is cleaved off, yielding the 84 amino acid mature hormone. Through its action on target cells in bone and kidney tubuli, hPTH increases serum calcium and decreases serum phosphate, while opposite effects are found regarding urinary excretion of calcium and phosphate. At chronically high secretory rates of PTH (hyperparathyroidism) bone resorption supersedes formation. However, prolonged exposure to low/moderate doses of a biologically active PTH-fragment stimulates bone formation and has also been reported to be effective in the treatment of osteoporosis by inducing an anabolic response in bone (Reeve et al. 1980 Br Med J 250, 1340–1344 Slovik et al. 1986 J Bone Min Ros 1, 577). So far studies on intact hPTH have been hampered by the limited availability and the high price of the hormone. Hence a system for the efficient expression of hPTH in microorganisms would be very advantageous for the further progression of studies on hPTH and its role in bone biology and disease.

Poly (A)+-selected RNA was isolated from human parathyroid adenomas immediately after surgery. The RNA was size frantionated, cDNA was prepared and cloned into the PatI site of pBR322 by the GC-tailing method. The library was screened by using synthetic oligonucleotides. Sixty-six clones of a total of 34,000 were found to be positive for both 5' and 3' PTH sequences. The correct identity of four of these clones was verified by DNA sequence analysis.

Employing the promoter and signal sequence of *Staphyloccous aureous* protein A we have expressed hPTH in *Escherichia coli* as a secretory peptide. Immunoreactive PTH was isolated both from growth medium and periplasmic space. We obtained up to 10 mg/l hPTH as judged by reactivity in radioimmunoassay.

hPTH was expressed in Saccharomyces cerevisiae after fusing hPTH cDNA to an expression vector coding for the prepro-region of the yeast mating factor $\alpha$. During the secretion process, the $\alpha$-factor leader sequence is cleaved off by an endopeptidase specific for a dibasic amino acid sequence and encoded by the KEX2 gene.

By hPTH-specific radioimmunoassay a significant amount of hPTH immunoreactive material was detected in the growth medium, corresponding to about 1 mg hPTH pr 1 medium, of the yeast strain FL200 transformed with fusion plasmid p$\alpha$LXPTH. No immunoreactive hPTH was secreted from cells transformed with the vector p$\alpha$LX.

Parallel cultures of the yeast strain FL200 transformed with one of the three expression plasmids pUCXPTH, p$\alpha$UXPTH-1 and p$\alpha$LXPTH with copy numbers near unity, normal high ($-30$) and very high ($>50$) respectively were grown and both grown medium, a periplasmic fraction and an intracellular soluble fraction were assayed for hPTH immunoreactive peptides.

The results show that the intermediate copy number gave the highest production. The produced PTH was secreted completely to the growth medium. The secreted products were concentrated from the growth medium and analyzed on SDS-PAGE. A distinct band with the same molecular weight as hPTH standard was visible on the gel.

hPTH immunoreactive material was concentrated from the growth medium by passage through a S Sepharose Fast flow column and eluted quantitatively. Recombinant hPTH was purified by reverse phase HPLC. The column was eluted with a linear gradient of acetonitrile/trifluoroacetic acid. A major peak fractions 32 and 33) with the same retention time as standard hPTH(1-84) was resolved into two peaks in a second HPLC urification step. The major peak from the 2.HPLC eluted exactly as standard hPTH(1-84) and co-chromatographed with hPTH(1-84) as one symmetric peak. SDS-PAGE of the peak fraction showed one band co-migrating with hPTH standard suggesting that the recombinant PTH was essentially pure. The recombinant hPTH was subjected to N-terminal amino acid analysis. We were able to determine unambiguously 45 amino acids from the N-terminal end in the *E. coli* protein and 19 amino acids in the yeast protein. The sequence was identical to the known sequence of hPTH. The sequence analysis indicated that the recombinant PTH was more than 90 percent pure. The recombinant hPTH from *E. coli* and *Saccharomyces cerevisiae* was fully active in adenylate cyclase assay and also induced hypercalcemia in rats after injection.

We have successfully expressed biologoically active intact human parathyroid hormone as a secretory peptide in *Escherichia coli* and *Saccharomyces cerevisiae*, and developed a down-stream purification technology.

BRIEF DESCRIPTION OF THE DRAWINGS

FIG. 1 shows all possible variations of the DNA sequence coding for human preproparathyroid hormone.

FIG. 2 shows the specific human preproparathyroid hormone DNA coding sequence of the clone pSSHPTH-10.

FIG. 3 shows a DNA sequence coding for human preproparathyroid hormone and having a double start codon at the 5' terminal end with flanking sequences in which are shown all possible variations of the DNA which may be present on the plasmid of the present invention.

FIG. 4 shows the specific human preproparathyroid hormone DNA coding sequence of the clone pSSHPTH-10 with flanking sequences.

FIG. 5 shows the actual amino acids sequence of the human preproparathyroid hormone for which the DNA sequence in close pSSHPTH-10 codes.

FIG. 6 shows the sequence of the MFα1-HPTH fusion gene with all possible combinations of the DNA coding for HPTH.

FIG. 7 shows the sequence of the MFα1-HPTH fusion gene.

Saccharomyces cerevisiae transformed with a PTH cDNA carrying plasmid was grown in liquid culture medium. The secreted products were concentrated and analyzed on SDS-PAGE. Panel a shown a silver stained gel with molecular size marker (lane S), hPTH standard and concentrated yeast growth medium (lane 1). After blotting onto a PVDF membrane, blots were probed with hPTH specific antibodies, one reactive against the aminoterminal part of the hormone (panel b), another reactive against the middle region of the hormone (panel c). Lanes in panel b and c are numbered as in panel a.

Figure 8:
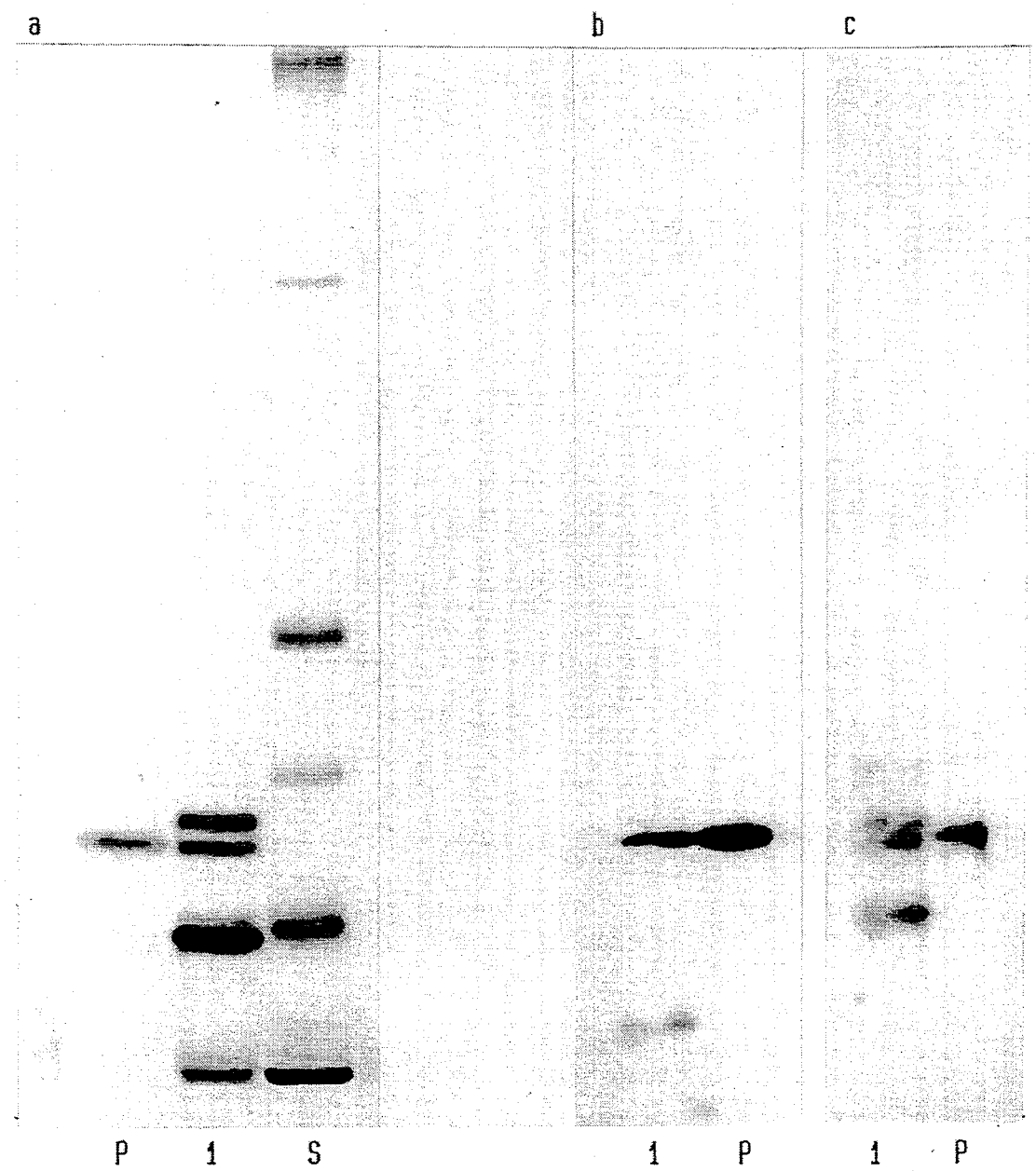
FIG. 8. Analysis of expression products by SDS-PAGE and immonoblotting.
Figure 9A:
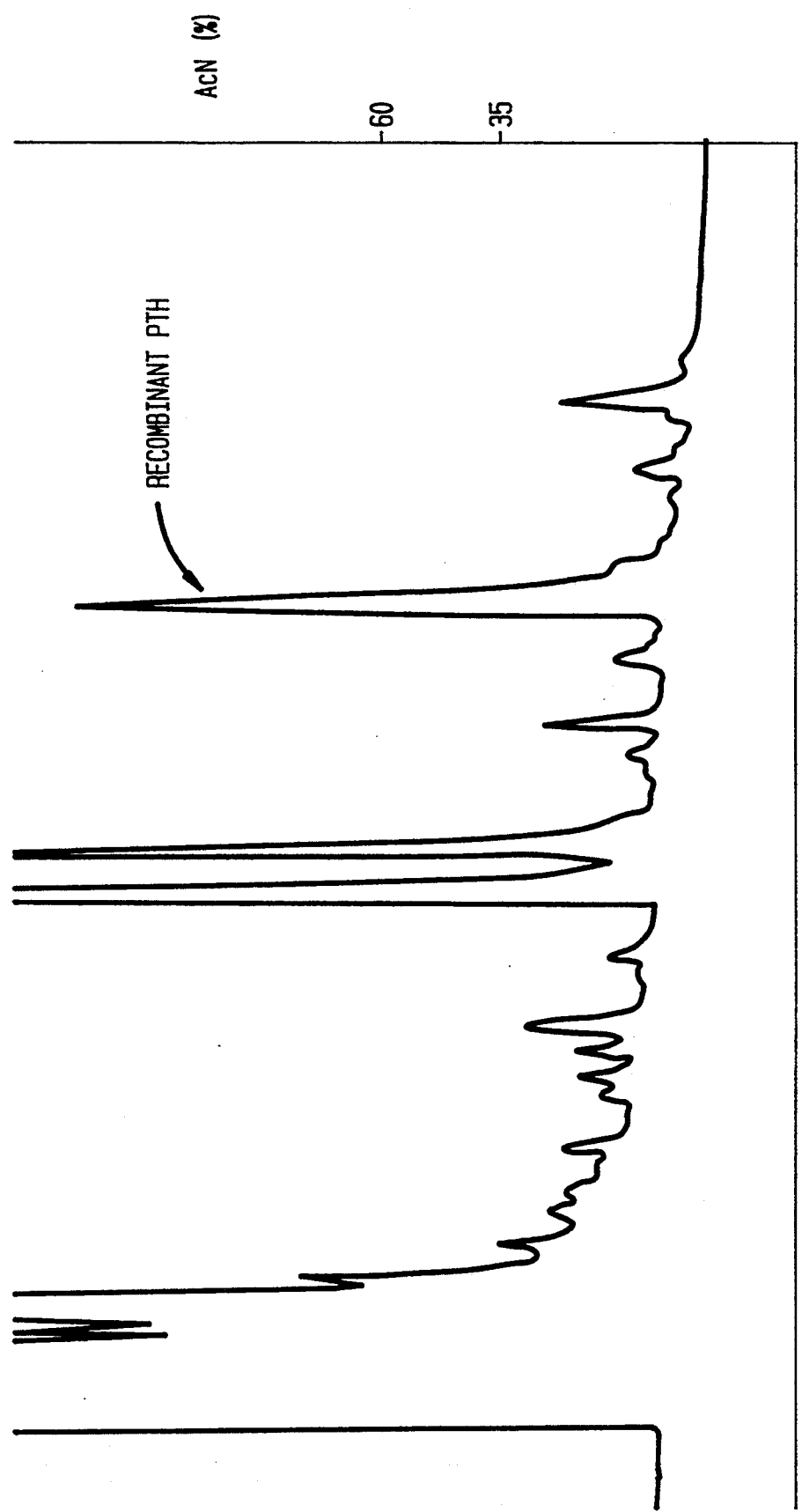
Figure 9B:
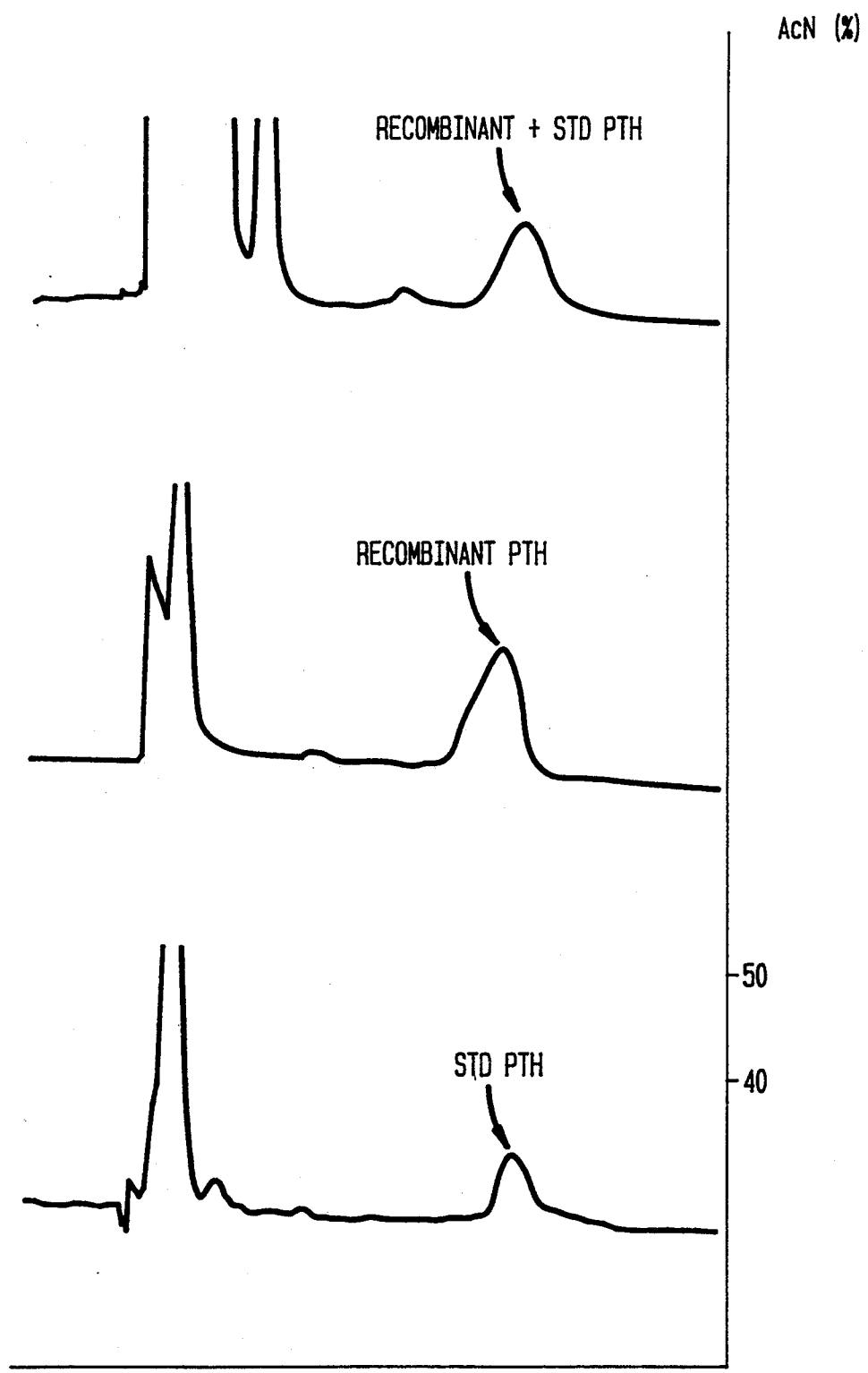

FIG. 9. Purification of recombinant hPTH from the growth medium.

A: Chromatogram of the 1.HPLC purification
B: Chromatogram of the 2.HPLC purification of fractions 32 and 33 from panel A. The peak of the recombinant hPTH is indicated by black.
C: 2.HPLC run of 1 ug standard hPTH(1-84)
D: Co-chromatography of the recombinant PTH pack from panel B and 1 ug of standard hPTH (1-84)
E: Silver staining of SDS-PAGE of the proteins in the hPTH pack
  1: recombinant hPTH, 1 ug
  2: hPTH(1-84) (r), 3ug (Note HMW Impurities)

Figure 10F:
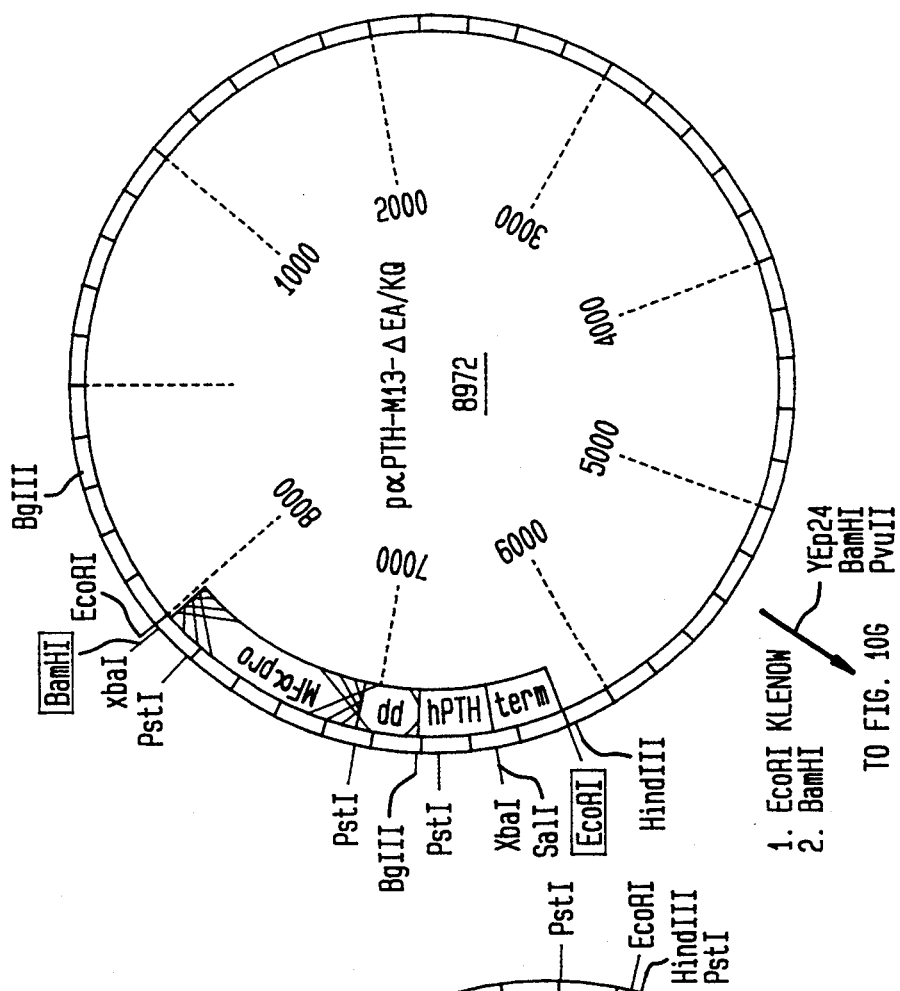
Figure 10E:
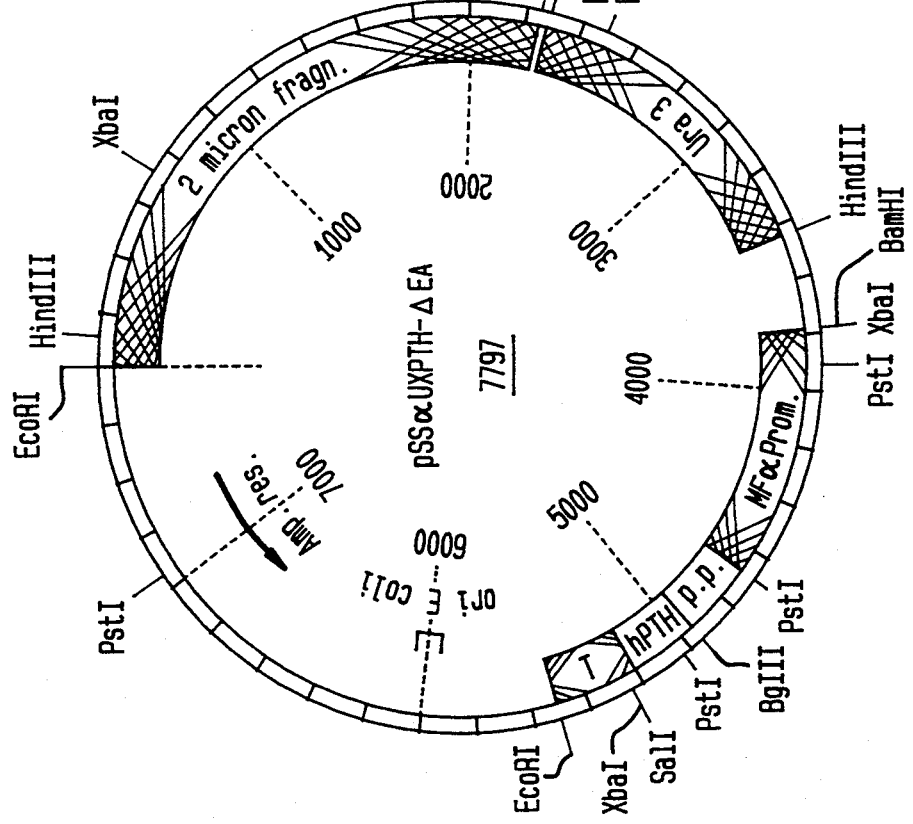
Figure 10G:
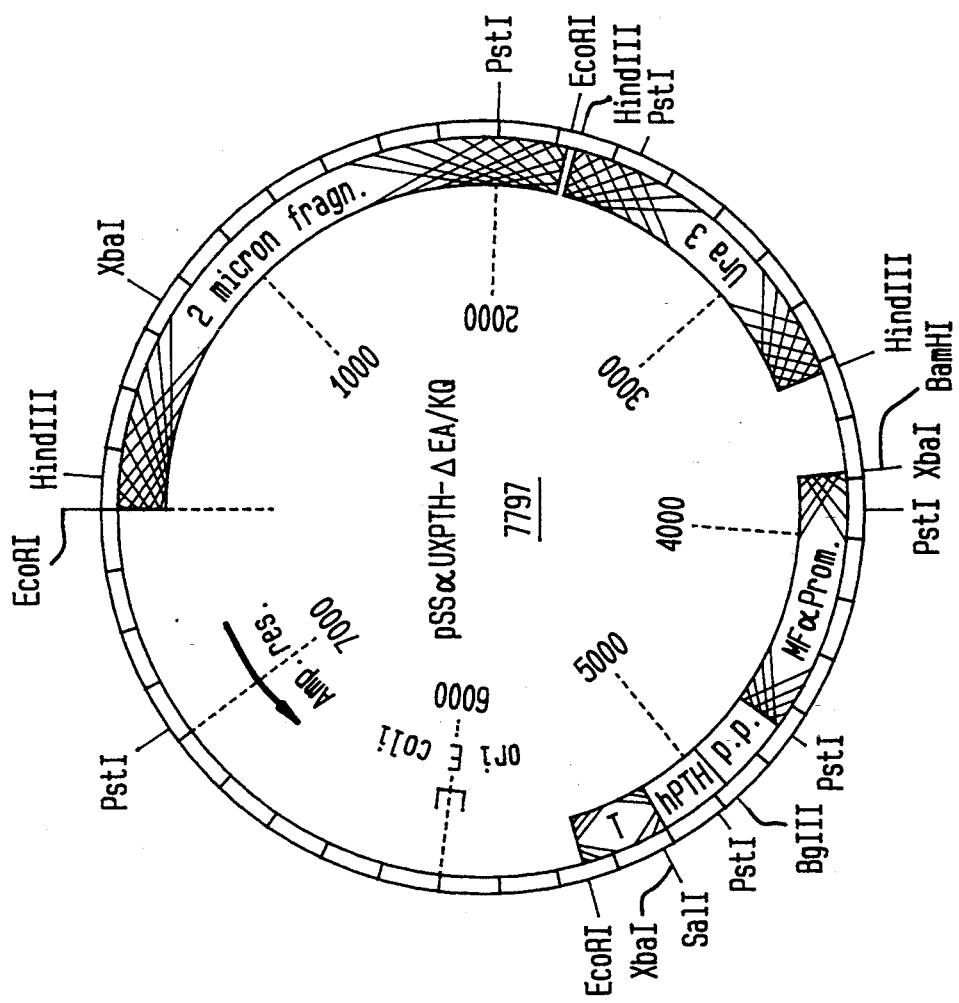

FIG. 10. Construction of pαPTH-M13-ΔEA/KQ.

Figure 11:
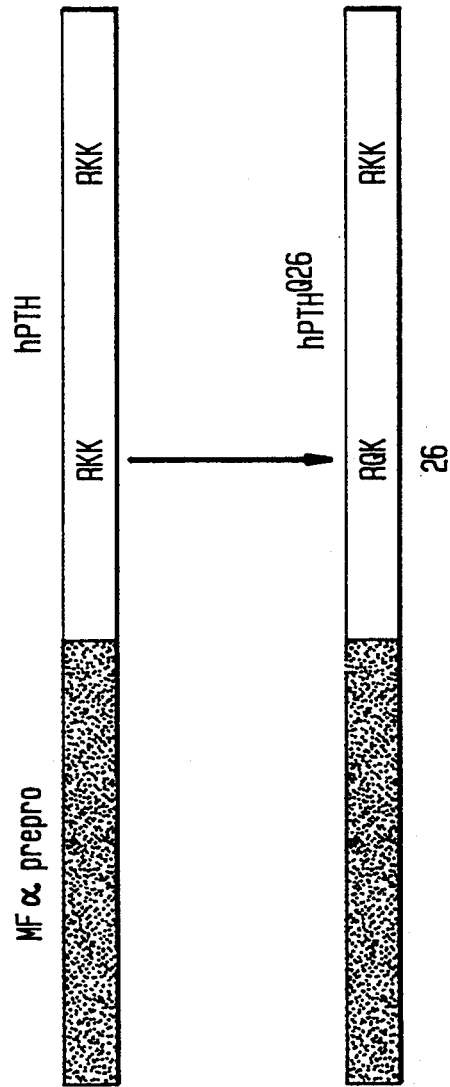

FIG. 11. Schematic representation of the mutation introduced in the gene fusion between the yeast α-factor prepro region and the human parathyroid hormone.

Figure 12:
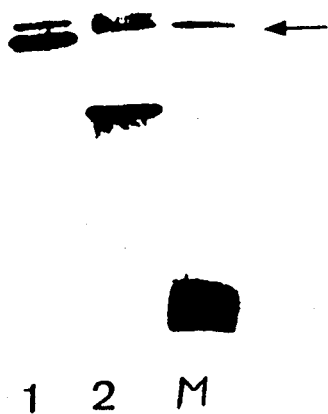

FIG. 12. SDS PAGE of concentrated yeast growth medium containing mutated and wild type hPTH. Aliquots of concentrated growth medium from yeast strain BJ1991 transformed with the expression plasmids pαUXPTH-2⁹ (lane 2) and pαUXPTH-Q26 (lane 1) were analyzed by 15% PAGE in the presence of 0.1% SDS, and visualized by silver staining as described in Experimental Protocol. Lane M shows a molecular size marker including a hPTH standard. The latter is marked with an arrow.

FIG. 13. Purity of purified hPTH (1-84,Q26). Yeast growth medium from yeast strain BJ1991 transformed with the expression plasmids pαUXPTH-Q26 were concentrated and purified by reversed phase HPLC as described in Experimental Protocol. The purity of the recombinant hormone was then analyzed by analytical HPLC (Panel A) and SDS PAGE (Panel B, lane 2). In Panel B the purified hPTH (1-84,Q36) is compared with the wild type hormone purified by two runs on HPLC (lane 3). The molecular weight market in lane M is the same as in FIG. 2. Lane 1 shows a reference PTH produced in E. coli.

Figure 14:
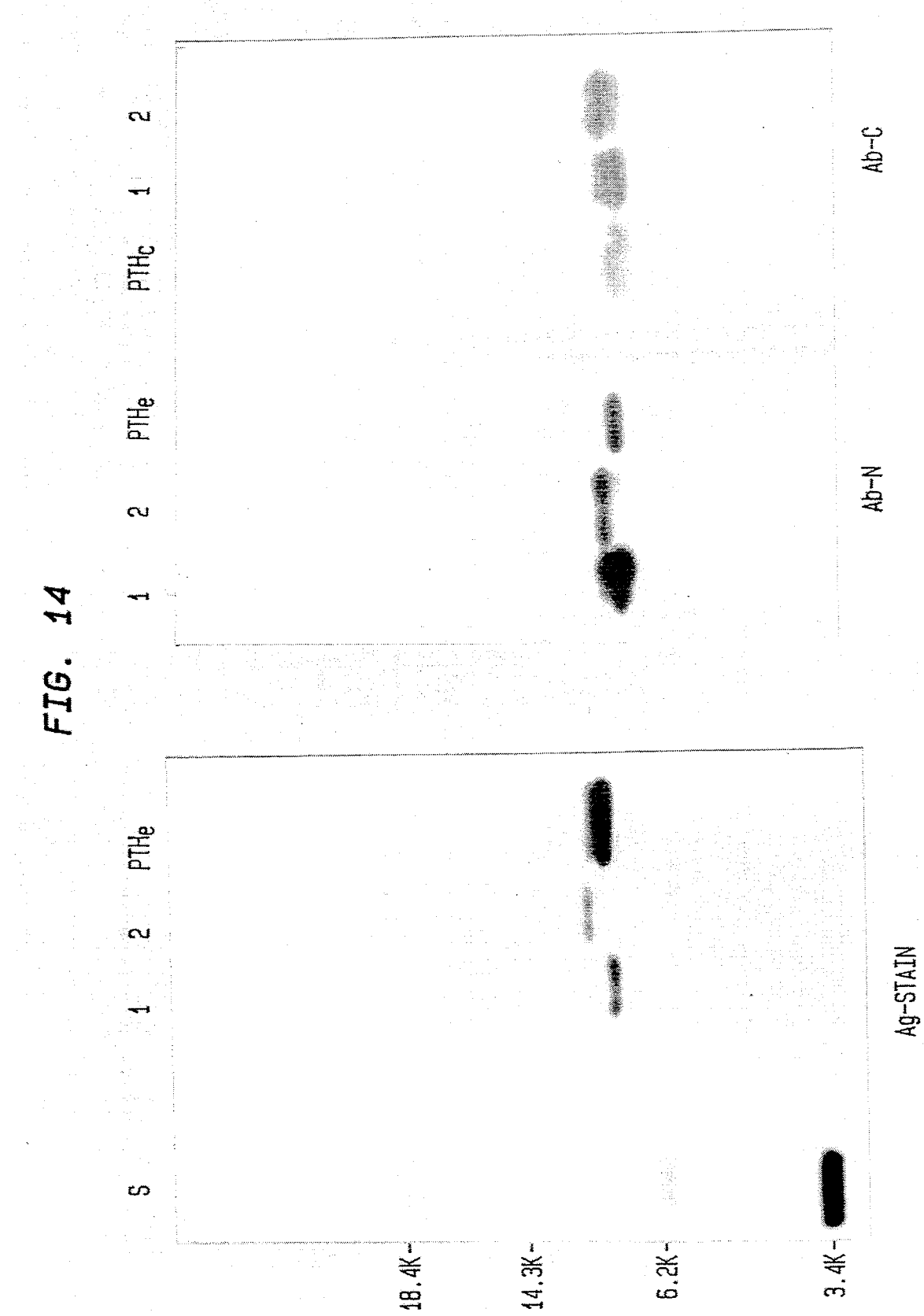

FIG. 14. Two dimensional gelelectrophoretic analysis of hPTH (1-84,Q26). An aliquot of concentrated growth medium from yeast strain BJ1991 transformed with the expression plasmids pαUXPTH-Q26 was separated on an acetic acid 15% PAGE. The two main bands (band 1 and 2) migrating close to the hPTH standard were then cut out, equilibrated with SDS loading buffer and run into a second dimension 15% PAGE containing 0.1% SDS in separate lanes in triplicate. This gel was divided in three and one part was colored with silver (Panel A), one part blotted and treated with hPTH N-terminal region specific antibodies (Panel B) and one part blotted and treated with hPTH middle-region specific antibodies (Panel C). Lanes 1 and 2 show band 1 and 2, $PTH_e$ is a reference hPTH produced in E. coli, $PTH_c$ is a commercial hPTH reference. Lane S shows a molecular weight standard.

Figure 15:
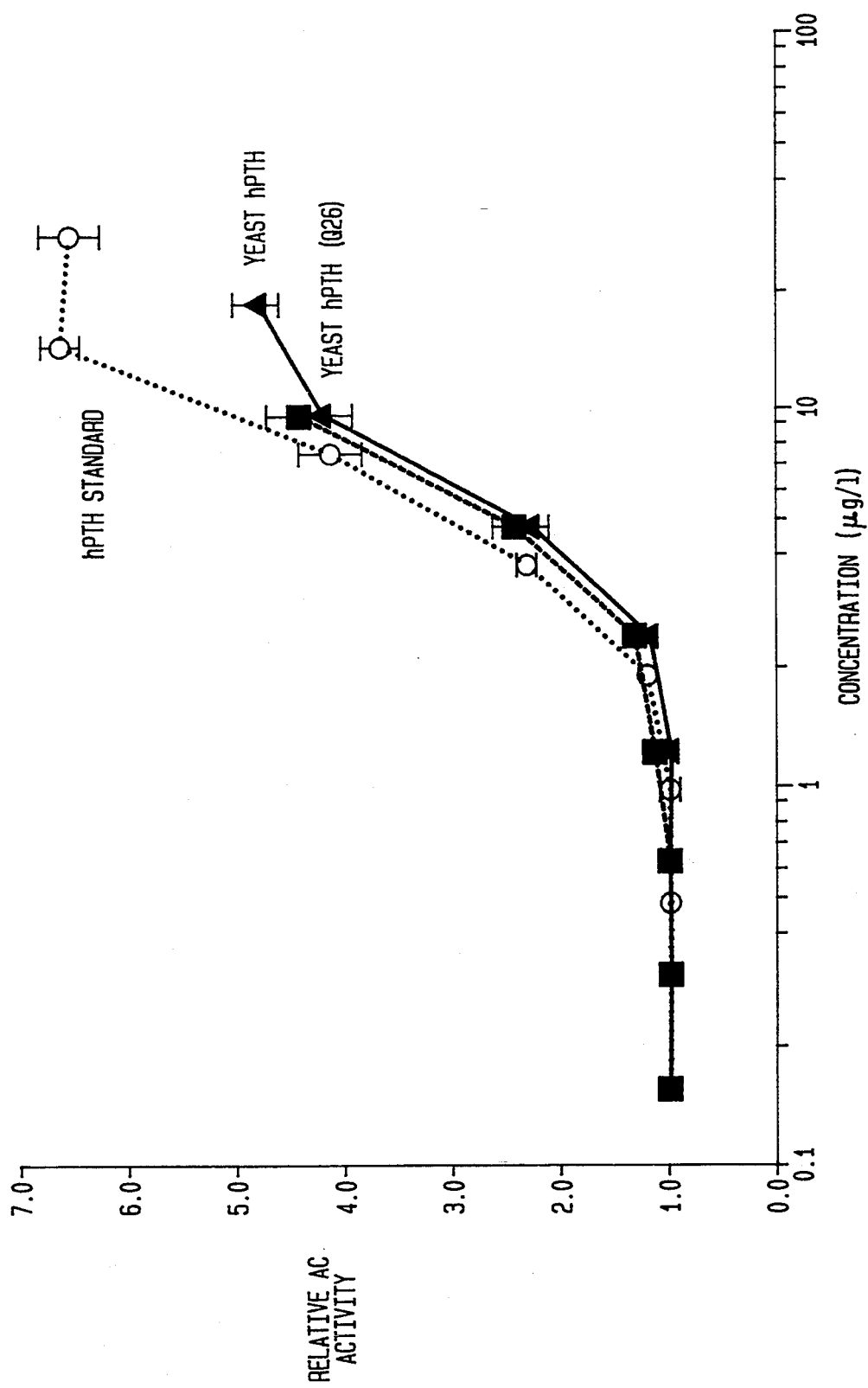

FIG. 15. Biological activity of hPTH (1-84,Q26). Recombinant hPTH (1-84,Q26) (□) was purified on HPLC and assayed for biological activity in a hormone-sensitive osteoblast adenylate cyclase (AC) assay as described in Materials and Methods. The experiments were carried out in triplicate determinations. hPTH (1-84) from Sigma (o) and recombinant yeast hPTH (1-84) (Δ) were used as references.

DETAILED DESCRIPTION OF THE PREFERRED EMBODIMENTS

Samples of pSS HPTH-10, E. coli transformed therewith, pSSLX5-HPTH1 and Saccharomyces cerevisiae transformed therewith were deposited in the American Type Culture Collection in Rockville, Md. on Sep. 29, 1986, under the provisions of the Budapest Treaty. The samples have been accorded the following deposit numbers.

As indicated above, the present invention is directed to a plasmid for insertion in E. coli containing DNA coding for human preproparathyroid hormone. The invention is also directed to the resulting transformed E. coli.

The invention further is directed to a plasmid for insertion into yeast which contains DNA coding for parathyroid hormone and which is derived from the plasmid for insertion into E. coli. Finally, the invention is directed to a transformed yeast from which parathyroid hormone may be recovered.

The invention further provides methods of producing and isolating the plasmids and transformed microorganisms. Poly(A) selected RNA was isolated from human parathyroid adenomas collected immediately after surgery. The poly(A) RNA was enriched for correct size mRNA by ultracentrifugation through sucrose gradients. Preproparathyroid hormone of correct molecular weight was translated in vitro from this size fractionated poly(A) RNA as judged by sodium dodecylsulphate polyacrylamide gel electrophoreses after immuno precipitation with antiparathyroid antiserum. The specific messenger RNA for the human PTH was used as template for complementary DNA synthesis using oligo d(T) 18 as a primer and avian myoblastosis virus reverse transcriptase. After removal of the RNA templates by alkali hydrolysis, the second strand complementary DNA was synthesized by incubating the purified first strand DNA in the presence of the Klenow fragment of E. coli DNA polymerase I. The double stranded comlementary DNA was made blunt ended by the action of Aspergillus oryzae single strand specific endonuclease S1 and complementary DNA longer than 500 base pairs was isolated after neutral sucrose gradient centrifugation. Approximately 20 bases long d(C)-tail protrusions were enyzmatically added to the 3 ends of the cDNA. This modified complementary DNA was annealed to restriction enconuclease PstI cleaved and d(G)-tailed vector pBR322. Resulting recombinant plasmid DNA's were transformed into E. coli KI2 BJ 5183. Positive transformants were analyzed for by colony hybridization using two different synthetic deoxyribo oligonucleotides which covered the N-terminal coding region as well as the 3' non-coding part of the hormone mRNA sequence, respectively. Six out of 66 clones that were positive for both probes were submitted for detailed analysis by restriction endonuclease mapping showing that they all were identical except for some size heterogenity at the regions flanking the start codon and the XbaI site 3' for the stop codon. One clone, pSSHPTH-10, was subjected to DNA sequence analysis revealing a 432 nucleotide long human parathyroid hormone complementary DNA sequence inserted in the PstI site of pBR 322. The entire cDNA sequence was found to be identical to the sequence previously described by Hendy, et al., supra, except for a 5 base pair deletion in front of the start codon.

FIG. 2 shows the human preproparathyroid hormone DNA sequence of pSSHPTH-10. This may be compared with FIG. 1, which shows all possible variations of the DNA sequence for human preparathyroid hormone without the 5' double start codon. FIG. 3 shows the DNA sequence of the clone of the present invention with the flanking sequences. In a preferred embodiment, the plasmid for insertion in E. coli coding for human preproparathyroid hormone is pSSHPTH-10, the DNA sequence of which, including the flanking sequence, is shown in FIG. 4.

The invention further provides a plasmid for insertion into yeast containing DNA coding for parathyroid hormone. The parathyroid hormone may be human or animal parathyroid hormone, for example pig or bovine parathyroid hormone. The plasmid for insertion in yeast of the present invention may be recloned from plasmids containing DNA coding for human or animal parathyroid hormone. In a preferred embodiment, the plasmid for insertion in yeast contains DNA coding for human parathyroid hormone. As shown in the following examples, the HTPH sequence from pSSHPTH-10 has been recloned and inserted in designed vectors for expression in Saccharomyces cerevisiae.

pSSHPTH-10 was digested to form a 288 bp BhlII-XbaI fragment. This fragment was then subcloned into pUC19 between the BamHI and XbaI sites. The subclone was then digested with Dpn I, and the largest resulting fragment was isolated. The said fragment was then digested with SalI.

The plasmid pSSαLX5-HPTH1 that in yeast MAT cells leads to the expression and secretion of PTH was constructed in three stages:
1. Construction of the yeast shuttle vector pL4 (which replicates in both E. coli and Saccharomyces cerevisiae).
2. Cloning of a DNA fragment containing the yeast mating pheromone MF 1 gene and its insertion into the yeast shuttle vector to make the p LX5 vector.
3. Insertion of a DNA fragment from the coding region of the HPTH gene of pSSHPTH-10 into pαLX5 in reading frame with the prepro part of the MFα1 gene, thereby producing the vector pSS LX5-HPTH1.

The shuttle vector pL4 was constructed by inserting into pJDB207, an EcoRI-AvaII fragment containing the ADHI promoter isolated from PADHO40. A SphI fragment was then deleted, resulting in a plasmid pALX1. The PstI site in the B-lactamase gene was deleted and the plasmid was partially digested with PvuI and BglI and ligated to a PvuI BglI fragment of pUCS, to form pALX2. After a further oligonucleotide insertion, the plasmid was digested with HindIII and religated to form pALX4.

Total yeast DNA from the Y288C strain was digested with EcoRI, and the 1.6–1.8 kb fragments isolated. These were ligated to EcoRI-cleaved pBR322, and E. coli was transformed. The clones were screened for MFα1 inserts by oligonucleotide hybridization. The DNA selected thereby was then used to transform E. coli. The resulting plasmid pMF 1-1 was digested with EcoRI, made blunt ended by Klenow enzyme, and then digested with BglII. The MFα1 fragment was isolated, and ligated to pL5 (digested with BamHI, made blunt ended with Klenow enzyme, and digested with BglII) to yield pαLX5.

In order to insert the human PTH cDNA fragment into pαLX5, the pαLX5 was digested with HindIII, creating sticky ends and the site was made blunt ended with the DNA polymerase I Klenow fragment and dNTP. The pαLX5 was then digested with SalI to create a sticky ended DNA complementary to the SalI digested human PTH fragment described above.

The SalI digested human PTH fragment was then inserted into the SAII digested p LX5. The resulting plasmid.

pSSαLX5-PTH was then inserted into yeast, thereby transforming yeast so that the yeast produces and secretes intact human parathyroid hormone. In a preferred embodiment, the transformed yeast is Saccharomyces cerevisiae.

As explained above, the invention provides alternate leader sequences which may be used for the production of parathyroid hormone or derivatives thereof, as taught by the present invention. The method set forth above discloses the use of the e-factor leader sequence. However, other sequences may be used, at least one of which has been shown to process PTH with greater efficiency than does the entire α-factor leader sequence. It has been discovered that the deletion from the α-factor leader of a 12-base sequence which comprises the yeast STE13 recognition site produces a more efficient production mechanism for PTH and/or its derivatives. The plasmid pSSα-UXPTH-ΔEA was constructed from pSS LX5-PTH. pSSαUXPTH-ΔEA contains the α-factor hPTH fusion gene placed between the α-factor promoter and terminator, in which the region encoding the Glu-Ala-Glu-Ala recognition sequence of the yeast STE13 aminopeptidase has been deleted. As another example of an alternative leader sequence, a leader sequence comprised of only the first nineteen amino acids of the α-factor is also used in the method of the present invention.

Also shown is an example of site specific mutagenesis changing the codon for the amino acid 26 in the PTH gene, thereby transforming a lysine-codon (K) to glutamine-codon (Q) using the Muta-Gene TM in vitro mutagenesis kit from Bio-Rad. For this purpose, the plasmid pαPTH-M13-ΔEA was used to transform the E. coli strain CJ236. A uracil-containing single-stranded DNA which was prepared from the phage was annealed to a synthetic oligonucleotide, and second strain synthesis was carried out with T4 DNA polymerase and ligation with T4 DNA ligase. The heteroduplex DNA was transformed into the E. coli strain MV1190 to be repaired into a homoduplex by removal of uracil incorporated in the parental strand. Positive clones were verified by DNA sequencing and one of these was called paPTH-M13-ΔEA/KQ. Finally, the entire expression cassette between a BamHI and a filled-in EcoRI site was isolated from this vector construction and inserted into the BamHI and PvuII site of the yeast shuttle vector YEp24 and this final expression plasmid was designated pSSaUXPTH-ΔEA/KQ.

A point mutation was introduced in the gene encoding the human parathyroid hormone leading to a change of the 26th amino acid from Lysine (K26) to Glutamine (Q26). When this gene was expressed and secreted in Saccharomyces cerevisiae using the e-factor fusion system, the full length hormone was found in the growth medium with no degradation products present. This contrasts the situation when the wild type gene is expressed in the same system. Then the major product is a hormone fragment hPTH(27-84), and only up to 20% of the immunoreactive secreted material is hPTH(1-84). The yield after a two step purification of the degradation resistant hormone was 5–10 fold higher than what was obtained with the wild type hormone. The secreted hPTH(1-84,Q26) had correct size, full immunological reactivity with two different hPTH specific antibodies and correct N-terminal amino acid sequence. Furthermore, the introduced mutation had no effect on the biological activity of the hormone as judged from its action in a hormone-sensitive osteoblast adenylate cyclase assay.

Human parathyroid hormone (hPTH) is one of the key calcium regulating hormones in the body. The hormone is produced in the parathyroid gland as a 115 amino acid prepropeptide that is processed during secretion to an 84 amino acid mature hormone.[1] It acts primarily on kidney and bone cells, stimulating calcium back resorption and calcium mobilization, respectively.[2-4] The hormone seems to exhibit differential catabolic as well as anabolic effects and its overall physiological action is probably to generate a positive calcium balance and enhance bone formation. The area of potential utility includes possible use in treatment of postmenopausal osteoporosis as well as in prevention of postpartum hypocalcaemia in cows. Sufficient supplies of authentic recombinant hPTH are of considerable interest to evaluate such applications.

hPTH is an easily degraded polypeptide. Already in the parathyroid gland large amounts of carboxyl-terminal PTH fragments are generated.[1] Structural studies have suggested that hPTH may contain two domains with the easily cleaved region placed in a connecting stalk between these domains.[5] Not surprisingly therefore, degradation of hPTH has been a major problem when the hormone is expressed in heterologous organisms. In E. coli low expression levels combined with degraded hormone peptides of short half-life were observed.[5-e,uns/8/] The most successful expression system for hPTH so far is Saccharomyces cerevisiae where the hormone is expressed as a secretory peptide.[9] By that approach we were able to obtain significant amounts of authentic hPTH(1-84) with full biological activity. But even if conditions were found which eliminated proteolytic attacks at some sites in the putative stalk region of the hormone, a significant fraction of the secreted peptides was still cleaved after a pair of basic amino acids found in the hPTH sequence reducing the yield of full length peptide hormone. The cleavage site resembles that recognized by the yscF protease (the KEX2 gene product).[10,11] We reasoned that the elimination of the putative yscF cleavage in hPTH could lead to a significant gain in the yield of undegraded hPTH secreted from yeast. In the present report we describe the removal of the putative yscF cleavage sites by in vitro mutagenesis of the hPTH coding region. When the amino acid at position 26 in hPTH was changed from Lysine (K26) to Glutamine (Q26), the major degradation product hPTH(27-84) previously observed disappeared in the growth medium and the yield of full-length hormone increased 5- to 10-fold. The secreted degradation resistant hPTH) 1-84, Q26) had correct size, full immunological reactivity with two different hPTH specific antibodies and correct N-terminal amino acid sequence. Furthermore, the introduced mutation had no effect on the biological activity of the hormone as judged from its action in a hormone-sensitive osteoblast adenylate cyclase assay.

The Saccharomyces cerevisiae strain used for the hPTH expression was BJ1991 (a, trp1, ura3-52, leu2, prb11122, pep4-3). Yeast cells were transformed by the lithium method[12], and transformants grown at 30° C. in YNBGC medium (0.67 percent yeast nitrogen base, 2 percent glucose, 1 percent casamino acids (Difco).

The paUXPTH-2 plasmid used as a reference for expression of authentic hPTH(1-84) is described.[9] In order to change the codon 26 in the hPTH gene from AAG (Lysine) to CAG (Glutamine), an a-factor hPTH gene fusion subcloned in M13 mp19 (designated M13PTH-3 in[9]) was modified by in vitro mutagenesis using the "Muta-gene ™ in vitro mutagenesis kit" (Bio-Rad) based on the method of Kunkel et al.[13]. The mutagenizing oligonucleotide had the sequence 5'-GGCTGCGTCAGAAGCTGC-3' where all nucleotides except the ninth are complementary to the actual hPTH sequence. Positive clones were verified by DNA sequencing.[14] One of those were picked and called M13PTH-Q26. The entire expression cassette between a BamHI and a filled in EcoRI site was finally isolated from M13PTH-Q26 and inserted between the BamHI and PvuII site of the yeast shuttle vector YEp24.[15] This expression plasmid was designated paUXPTH-Q26. The translation product from the hPTH gene between amino acid 25 and 27 should now change from Arg-Lys-Lys to Arg-Gln-Lys.

Radioimmunoassay of hPTH in yeast culture media was carried out as described.[9,16]. For electrophoretic analysis, yeast culture media were concentrated as previously described[9], and separated on a 15 percent polyacrylamide gel in the presence of SDS[17], and either stained with silver[18] or further analyzed by protein blotting using Immobilon PVDF Transfer Membranes (Millipore) and the buffers of Towbin et al.[19] Reference hPTH(1-84) was purchased from Peninsula Laboratories (USA). Protein blots were visualized as described.[9]

The concentrated medium from the Sepharose S column was subjected to further purification by reversed phase HPLC using a Vydac protein peptide C18 column (The Separation Group, Hesperia, Calif., USA). The column was eluted with a linear gradient of acetonitrile/0.1 percent trifluoroacetic acid.

Proteins to be sequenced was purified either by HPLC as described above or by SDS polyacrylamide gelelectrophoresis followed by blotting onto polyvinylidene difluoride membranes.[20] Automated Edman degradation was performed on a 477A Protein Sequencer with an on-line 120A phenylthiohydantoin amino acid analyzer from Applied Biosystems (Foster City, Calif., USA). All reagents were obtained from Applied Biosystems.

The adenylate cyclase stimulating activity of the recombinant hPTH was assayed as previously described[9,21,22] hPTH(1-84) from Sigma was used as reference.

Different strategies could be envisaged to avoid the degradation of parathyroid hormone during expression in heterologous organisms. One recently reported strategy is to express intracellularly in E. coli a cro-lacZ-hPTH fusion protein that subsequently is cleaved by strong acid to give proline-substituted hPTH.[23] However, since secretion of the hormone in yeast seems to be a more efficient way of producing a correctly processed hormone, and also is superior with respect to downstream processing, we rather adopted a strategy to improve this system. Only one major cleavage site is used during secretion in yeast when the cells are grown under proper conditions: after a pair of basic amino acids in position 25 and 26 in the hPTH sequence. This cleavage site resembles that recognized by the yscF protease (the KEX2 gene product). We reasoned that a substitution of a glutamine for the lysine 26, as illustrated in FIG. 11, ought to be a structurally conservative change that should exclude the hormone as a substrate for the yscF protease.

The yeast strain BJ1991 was transformed with the plasmids paUXPTH-Q26 containing the mutated hPTH coding region. One transformant was grown in YNBGC medium lacking uracil and the cell free medium was concentrated and analyzed in different gel systems. FIG. 12 shows a silver-stained SDS polyacrylamide gel where concentrated medium from paUXPTH-Q26 transformed cells (mutated hPTH, lane 1) is compared with that from paUXPTH-2 transformed cells (wild type hPTH, lane 2). In the latter case the strongest band has a molecular mass lower than the standard hPTH, and previous microsequencing has shown that it corresponds to the hormone fragment hPTH(27-84). In the lane with the mutated product (lane 1), this band is absent showing that the cleavage between amino acid 26 and 27 has been totally eliminated as a result of the mutation. Now the major product is a polypeptide that migrates close to the full length hPTH standard. Consistently, this band had a migration slightly faster than the standard in an anionic gel system and a migration slightly slower than the standard in a cationic gel system in accordance with the single charge difference between the mutated (one positive charge less) and the wild type hormone. In addition to the main product a few weaker bands were present of apparently higher molecular mass which might be O-glycosylated forms of the hormone.

This hPTH(1-84,Q26) candidate was further analyzed by two dimensional gel electrophoresis and protein blotting. In the first dimension acetic acid/urea gel a simple pattern with mainly two bands was found. These were cut out and run on a second dimension SDS polyacrylamide gel. The silver stained second dimension gel as well as two protein blots probed with different PTH antibodies, are shown in FIG. 14. The hPTH(1-84,Q26) candidate migrating closest to the hPTH standard in both dimensions, reacted with two hPTH specific antibodies raised against N-terminal region and the middle/C-terminal region of the hPTH respectively.

The nature of the hPTH(1-84,Q26) candidate was finally confirmed by N-terminal amino acid sequencing, both directly on the polypeptide band after blotting onto a PVDF membrane filter, and after purification on reversed phase HPLC. Correct amino-terminal sequence was found in both cases. Furthermore, the expected change from lysine to glutamine in position 26 was confirmed by sequencing through this position.

Figure 13A:
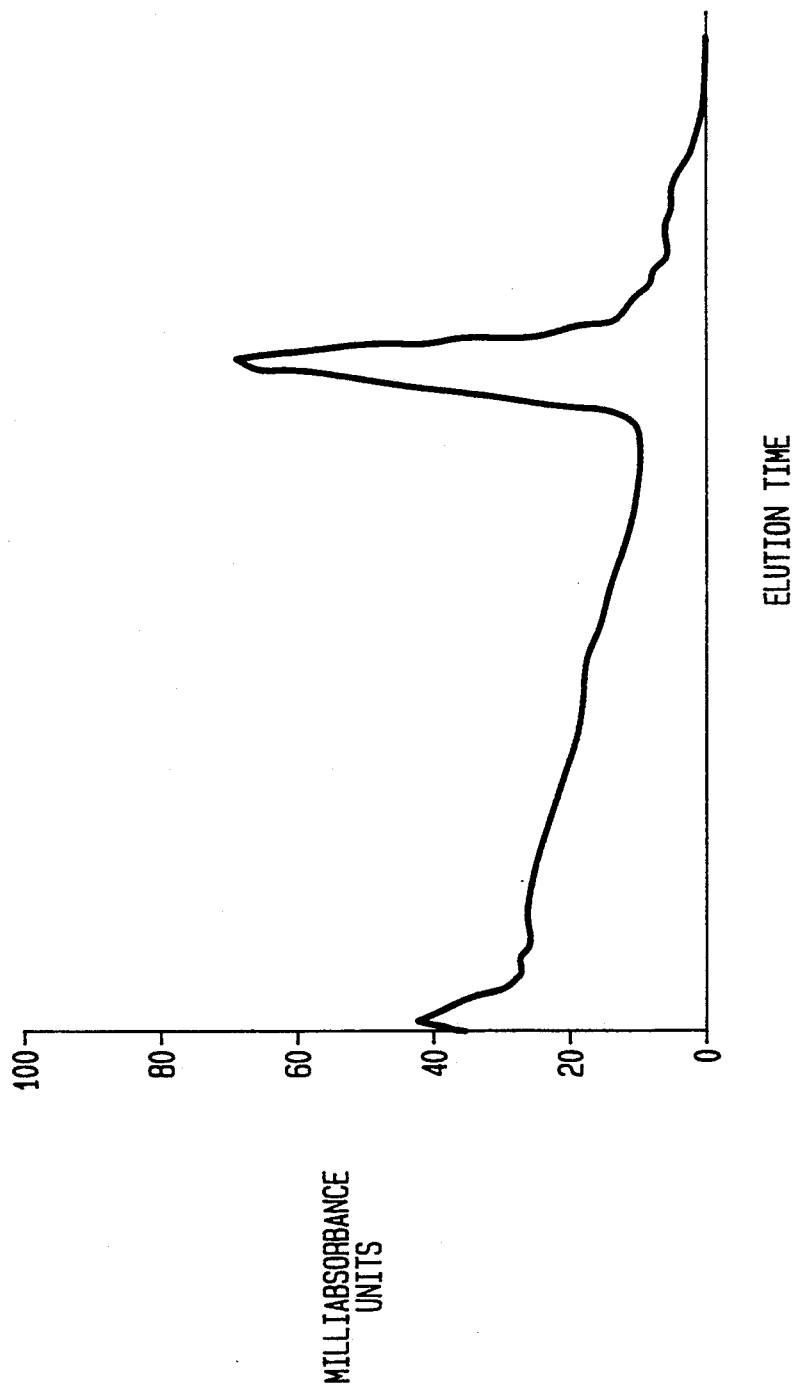
Figure 13B:
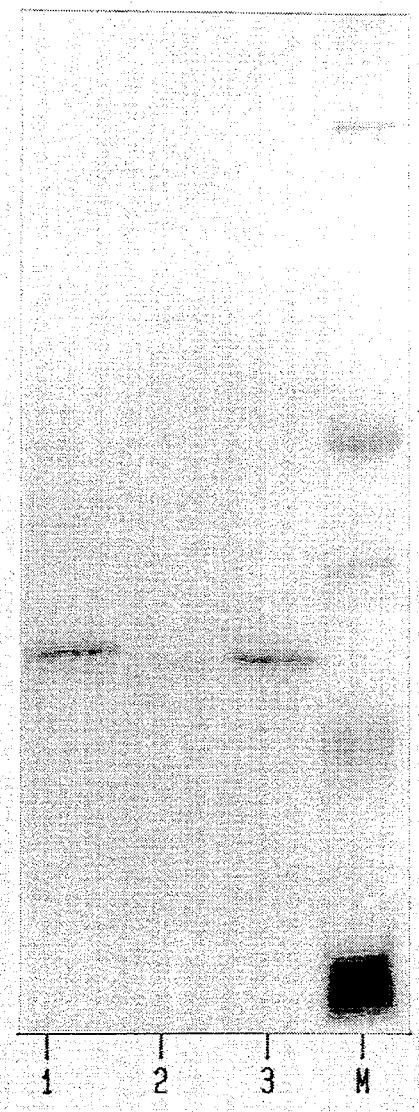

Since the elimination of the internal cleavage of the secreted hPTH leads to fewer polypeptides with similar properties in the growth medium, this form of the hormone could also be isolated by a simplified purification procedure. Already in the first concentration step using a Sepharose S column, a certain purification is achieved. All hPTH immunoreactive material is retained, but some high molecular weight material is removed in the pH6 wash of the Sepharose S column. This first concentrated eluate already contained more than 80 percent hPTH(1-84, Q26). Then, a single run on a reversed phase HPLC C18 column, was enough to give near homogeneous hPTH(1-84, Q26). The purity was checked both by SDS polyacrylamide gelelectrophoresis and sensitive silver-staining, and by analytical HPLC as illustrated in FIG. 13A. A single peak is found in the chromatogram (FIG. 13A), and a single band with only a trace of a closely migrating hPTH band (probably an O-glycosylated form of the hormone) could be seen in the SDS polyacrylamide gel (FIG. 13B). When the yield of pure full length mutated hormone was compared with that of the wild type, 5 to 10 fold higher yields were usually achieved. This is consistent with our previous estimate of the fraction of full length hormone (up to 20 percent) obtained when the wild type is expressed.[9]

The biological activity of the secreted hPTH(1-84, Q26) was tested in a hormone-sensitive osteoblast adenylate cyclase assay.[9,21,22] The purified hPTH(1-84, Q26) was analyzed for its ability to stimulate the adenylate cyclase activity of OMR 106 osteosarcoma cells above the basal level. The quantitative analysis shown in FIG. 15, clearly demonstrates that hPTH(1-84, Q26) has a stimulatory effect comparable to that of a commercial hPTH control. The stimulation curve practically coincides with that of purified recombinant wild type hPTH(1-84). Consequently, no difference in biological activity could be detected between the wild type hormone and the degradation resistant mutated hormone.

We have shown that the easily degraded human parathyroid hormone can be expressed in a correctly processed and intact form in Saccharomyces cerevisiae after the introduction of a single, structurally conservative mutation in the 26th amino acid of the hormone. The increase in final yield of pure full length hormone is 5- to 10-fold compared to what is obtained with wild type hormone expressed in the same system. The mutation also simplifies the downstream purification of the hormone. A concentration step followed by a single HPLC run was enough to give near homogeneous recombinant hormone.

We have previously described conditions of growth that eliminates secondary cleavages in the protease sensitive "stalk" region of the hormone[9]. Here we describe how the final dibasic cleavage site can be eliminated. After introduction of the mutation, a form of the hormone is produced that totally resists the frequent cleavage found in the wild type hormone after the Arg25-Lys26 motif. The possible internal cleavage at putative dibasic amino acids is one of the severe drawbacks of the α-factor secretion system. To our knowledge this is the first reported case where this problem has been successfully overcome.

Previous reports have shown that the biological activity of the hormone resides in the first third of the molecule in a minimum structure comprised of amino acids 1-27. Furthermore, the triple basic amino acid motif from position 25-27 seems to be conserved between the bovine25, porcine26 and human hormone27. It was therefore not obvious that the introduction of a mutation in position 26 would not destroy the biological activity of hPTH. However, no difference between the recombinant hPTH products could be detected in the adenylate cyclase assay, showing that the introduced mutation does not affect the biological activity of the hormone.

hPTH is a multifunctional hormone with many potential uses, for example in diagnostics and as a drug in veterinary medicine. A fragment of hPTH together with 1,25(OH)$_2$ vitamin D$_3$ has also been reported to induce bone formation in humans [28, 29] and one of the major areas of potential use of a recombinant hPTH is therefore in the treatment of osteoporosis. To evaluate such applications, sufficient supplies of recombinant hPTH are essential. In the present report we have described what we believe is the most efficient way of producing full length biologically active parathyroid hormone so far.

Moreover, the method of the present invention may be used to produce parathyroid hormone derivatives having parathyroid hormone agonistic or antagonistic activity. These derivatives include hormone analogs, such as the example described above in which the lysine at position 26 is substituted with glutamine, or may be fragments or extensions of the hormone, i.e., polypeptides having parathyroid hormone agonist or antagonist activity which are respectively shorter or longer than the hormone itself. Parathyroid hormone agonistic effect in this connection will be demonstrated by activation of adenylyl cyclase in bone cells and kidney cells. The in vivo effects of such activity mimic the effects of native parathyroid hormone with respect to plasma calcium concentration alterations as well as the well known hormonal actions on calcium and phosphate re-absorption and excretion in the kidney. Furthermore, the PTH derivatives of the present invention having agonist activity shall also have the capacity to reduce the alkaline phosphatase activity of certain osteoblast cell lines, and stimulate ornithine decarboxylase activity bone cells (UMR 106 cells) or chicken condrocytes and stimulate DNA synthesis in chicken condrocytes. Moreover, the derivatives shall have the capability of blocking the action of parathyroid hormone itself or of any of the other agonist derivatives.

The invention also provides alternate secretion signal seqences for the secretion of the PTH hormone or its derivatives from yeast. As disclosed above, parts of the MFα1 gene may be inserted into the plasmid of the present invention to cause the yeast to secrete the intact PTH hormone or derivatives. However, other signal sequences will also function in the methods of the present invention. The process of protein secretion requires the protein to bear an amino-terminal signal peptide for correct intracellular trafficking, the sequence of which is termed "signal sequence". Two classes of signal sequences will function in the plasmids of the present invention, and will cause secretion of the PTH hormone or derivative from yeast: "optimalized consensus signal sequences" and other functional signal sequences. An "optimalized consensus signal sequence" is any amino-terminal amino acid sequence that is composed of the following three parts:

1. An amino-terminal positively charged region. The size of this region may vary from 1-20 amino acids. The only specific characteristic is a positive charge at physiological pH conferred by the presence of one to three basic amino acids (Lys or Arg).
2. A hydrophobic core region. The size of this region may vary from 7-20 amino acids, and it is predominantly composed of hydrophobic amino acids (Phe, Ile, Leu, Met, Val, Tyr, or Trp).
3. A polar COOH-terminal region composed of five amino acids (from position $-5$ to $-1$ relative to the cleavage site) that defines the cleavage site. The specific character of this region is that the amino acid in position $-1$ must be a small neutral amino acid (Ala, Ser, Gly, Cys, Thr, or Pro), and that the amino acid in position $-3$ must be either a hydrophobic amino acid (Phe, Ile, Leu, Met, Val) or a small neutral amino acid (Ala, Ser, Gly, Cys, Thr, or Pro).

See von Heijne, G. (1983) "Patterns of Amino Acids near Signal-Sequence Cleavage Sites." *Eur. J. Biochem.* 133, 17-21, and von Heijne, G. (1985) "Signal sequences. The limits of variation." *J. Mol. Biol.* 184, 99-105. However, Kaiser, C. A., Preuss, D., Grisafi, P., and Botstein, D. (1987) "Many Random Sequences Functionally Replace the Secretion Signal Sequence of Yeast Invertase." *Science* 235, 312-217, found the specificity with which signal sequences were recognized in yeast to be low and that any amino-terminal peptide with a hydrophobicity above some threshold value would function. Therefore, "functional signal sequence" is defined as any amino-terminal amino acid sequence that can direct secretion in yeast even if it does not fit all the criteria of an optimal signal sequence.

Specific examples of signal sequences functional in yeast that conform to the description of an optimal signal sequence are:

1. Met,Lys,Ala,Lys-Leu,Leu,Val,Leu,Leu,Thr,Ala,Phe-Val,Ala,Thr,Asp,Ala (Jabbar, M. A., and Nayak, D. P. (1987) "Signal Processing, Glycosylation, and Secretion of Mutant Hemagglutinins of a Human Influenza Virus by Saccharomyces cerevisiae." *Molec. Cell, Biol.* 7, 1476-1485.) from a human influenza virus hemagglutinin.
2. Met,Arg,Ser-Leu,Leu,Ile,Leu,Val,Leu,Cys,Phe,Leu,Pro-Leu,Ala,Ala,Leu,Gly (Jigami, Y., Muraki, M., Harada, N., and Tanaka, H. (1986) "Expression of synthetic human-lysozyme gene in *Saccharomyces cerevisiae*: use of a synthetic chicken-lysozyme signal sequence for secretion and processing." Gene 43, 273-279.) from chicken lysozyme.
3. Met,Arg,Phe,Pro,Ser-Ile,Phe,Thr,Ala,Val,Leu,Phe,Ala,Ala-Ser,Ser,Ala,Leu,Ala (Ernst, J. F. (1988) "Efficient Secretion and Processing of Heterologous Proteins in Saccharomyces cerevisiae is mediated solely by the Pre-Segment of α-factor Precursor." DNA 7, 355-360. Kurjan, J. and Herskowitz, I. (1982) "Structure of a Yeast Pheromone Gene (MFa): "A putative α-factor Precursor contains four Tandem Copies of Mature α-factor". *Cell* 30, 933-934.) from yeast α-factor precursor.

A specific example of signal sequences functional in yeast that conforms to the description of a functional signal sequence is Met,Asn,Ile,Phe,Tyr,Ile,Phe,Leu,-Phe,Leu,Ser,Phe,Val-Gln,Gly, Thr,Arg,Gly. Baldari, C., Marray, J. A. H., Ghiara, P., Cesareni, G., and Caleotti, C. L. (1987) "A novel leader peptide which allows efficient secretion of a fragment of human interleukin 1B in Saccharomyces cerevisiae."*EMBO J.* 6. 229-234. from Klyveromyces lacis killer toxin.

Finally, the invention provides three different steps which taken together, represent an effective and convenient procedure for purification of human recombinant parathyroid hormone (PTH). A cation exchange chromatography using S-Sepharose column as described in the text, washed at pH 6 and eluted at pH 8.5. The immunoreactivity of the intact PTH migrates within the peak.

FIG. 10 shows high performance liquid chromatography (HPLC) of hPTH which was eluted with trifluoraecetic acid and a linear gradient of acetonitril of 35-60%. The position of intact PTHh is indicated in the second HPLC step the acetonitril gradient has been changed to 40-45% and intact PTHh elutes as one symmetrical peak.

Although the methods of making the invention disclosed herein are shown in detail, these methods are presented to illustrate the invention, and the invention is not limited thereto. The methods may be applied to a variety of other plasmids containing DNA coding for human or animal PTH to produce the plasmids for insertion in yeast of the present invention.

The plasmids of the present invention and transformed microorganisms were produced as set forth in the following examples.

EXAMPLE 1

Isolation of mRNA and synthesis of complementary DNA (cDNA) of human parathyroid hormone starting material for the invention was parathyroid adenomas obtained from patients by surgery. The parathyroid tissue was placed on dry ice directly after removal and transported to a laboratory for preparation of RNA. The frozen tissue was homogenized with an ultra Turax homogenizer in the presence of 4 M Guanidinium thiocyanate and the RNA content was recovered by serial ethanol precipitations as described by Chirgwin, J. M., Przybyla, A. E., MacDonald, R. J. and Rutter, W. J., 18 *Biochemistry* 5294-5299 (1979). The RNA preparation was applied to oligo d(T) cellulose affinity chromatography column in order to enrich for poly(A) containing mRNA. The poly(A) rich RNA was further enriched for parathyroid hormone (PTH) mRNA sized RNA by ultracentrifugation through a 15-30% linear sucrose gradient. The resulting gradient was divided into 25 fractions and every third fraction was assayed for PTH mRNA content by in vitro translation followed by immunoprecipitation with anti PTH antiserum (Gautvik, K. M., Gautvik, V. T. and Halvorsen, J. F., *Scand. J. Clin. Lab, Invest.* 43, 553-564 (1983)) and SDS-polyacrylamide gel electrophoresis (Laemmeli, U. K., 227 *Nature* 680 (1970)). The RNA from the fractions containing translatable PTH mRNA was recovered by ethanol precipitation. This RNA, enriched for PTH mRNA, was used as a template for cDNA synthesis using oligo d(T) 18 as a primer and avian myoblastosis virus reverse transcriptase for catalysis of the reaction (Maniatis, T., Fritsch, E. F. and Sambrook, J., *Molecular Cloning* pp. 230-243 (1982)). After first strand synthesis, the RNA templates were removed by alkali hydrolysis. The second strand cDNA was synthesized by incubating the purified first strand cDNA in the presence of the Klenow fragment of *E. coli* DNA polymerase I (Maniatis, supra). This in vitro synthesized double stranded cDNA was made blunt ended by the action of Aspergillus oryzae single strand specific endonuclease S1 (Maniatis, supra). The blunt ended double stranded cDNA was size fractionated over a 15-30% neutral sucrose gradient. The size distribution of each fraction was estimated by agarose gel electrophoresis together with known DNA fragment markers. Fractions containing cDNA larger than approximately 500 base pairs were pooled and the cDNA content was collected by ethanol precipitation.

EXAMPLE 2

Cloning of cDNA PTH in plasmid pBR 322 and transformation of *E. coli* K12 BJ5183.

An approximate 20 base long d(C)-tail protrusion was enzymatically added to the 3' ends of the cDNA by the action of terminal deoxynucleotidyl transferase (Maniatis, supra). The d(C)-tailed cDNA was annealed to restriction endonuclease Pst I cleaved and d(G)-tailed vector pBR322 and the resulting recombinant plasmid DNA's were transformed into *E. coli* K12 BJ 5183 cells which were made competent by the method of Hanahan, D., 166 *J. Mol. Biol.* 166, 557-580 (1983). A total of 33,000 transformants were analyzed for PTH cDNA content by colony hybridization (Hanahan, D. and Meselson, *Gene* 10, 63 (1980)).

Two to three thousand transformants were plated directly on each 82 mm diameter nitrocellulose filter, placed on top of rich medium agar plates containing tetracycline, and incubated at 37 degrees Centigrade until approximately 0.1 mm diameter colonies appeared. Duplicate replicas of each filter was obtained by serial pressing of two new filters against the original filter. The replica filters were placed on top of new tetracycline containing agar plates and incubated at 37 degrees Centigrade until approximately 0.5 mm diameter colonies appeared. The master filter with bacterial colonies was kept at 4 degrees Centigrade placed on top of the agar plate and the duplicate replica filters were removed from the agar plates and submitted to the following colony hybridization procedure.

EXAMPLE 3

Characterization of bacterial clones containing recombinant cDNA PTH and of the DNA sequence of clone pSSHPTH-10

The cells in the respective colonies were disrupted in situ with alkali and sodium chloride leaving the DNA content of each bacterial clone exposed. The procedure allows the DNA to bind to the filter after which it was neutralized with Tris-buffer and dried at 80 degrees Centigrade. The majority of cell debris was removed by a 65 degree Centigrade wash with the detergent sodium dodecylsulphate (SDS) and sodium chloride leaving the DNA bound to the filters at the position of the former bacterial colonies. The filters were presoaked in 6xSSC (0.9 M NaCl, 0.09M Na-citrate), 1x Denhart's solution (0.1 g/ml FIcoll, 0.1 g/ml polyvinyl pyrrolidone, 0.1 g/ml bovine serum albumin), 100 g/ml herring sperm DNA, 0.5% SDS and 0.05% sodium pyrophosphate for 2 hours at 37 degrees Centigrade (Woods, D. E. 6 *Focus* Vol. No. 3. (1984)).

The hybridization was carried out at 42 degrees Centigrade for 18 hours in a hybridization solution (6x SSC, 1x Denhart's solution, 20 g/ml tRNA and 0.05% sodium pyrophophate) supplemented with 32P-labelled DNA probe (Woods supra).

The DNA used as a hybridization probe was one of two different synthetic deoxyribo oligonucleotides of which the sequences were deduced from the published human PTH cDNA sequence of Hendy, supra. The first probe was a 24-mer oligonucleotide originating from the start codon region of the human preproPTH coding sequence having a nucleotide sequence reading TAC-TATGGACGTTTTCTGTACCGA. The second oligonucleotide was a 24-mer spanning over a cleavage site for the restriction endonuclease XbaI located 31 nucleotides downstream of the termination codon and consisted of the nucleotide sequence CTCAAGAC-GAGATCTGTCACATCC.

Labelling was carried out by transfer of 32 P from 32 P-γ-ATP to the 5' end of the oligonucleotides by the action of polynucleotide kinase (Maxam, A. M. and Gilbert, W., 65 *Methods Enzymol.*, 499 (1980)).

The hybridized filters were washed in 6xSSC, 0.05% sodium pyrophosphate at 42 degrees Centigrade prior to autoradiography. Sixty-six clones were found to be positive for both probes as judged from hybridization to both copies of the duplicate replica filters. All those were picked from the original filters with the stored cDNA library and amplified for indefinitive storage at −70 degrees Centigrade. Six of these were chosen for plasmid preparation and a more detailed analysis by restriction endonuclease mapping, showing that all were identical except for some size heterogenity at the regions flanking the start codon and Xba I site, respectively.

EXAMPLE 4

Clone pSSHPTH-10

One clone, pSSHPTH-10, was subjected to DNA sequence analysis according to the method of Maxam and Gilbert, supra. This clone consists of a 432 base pair long PTH cDNA sequence inserted in the Pst I site of pBR322 having 27 G/C base pairs at the 5' end and 17 G/C base pairs at the 3' end. The complete DNA sequence of the cDNA insert of pSSHPTH-10 is shown in FIG. 4. It is identical to the sequence of Hendy, et al., supra except for a five base pair deletion right in front of the start codon, changing the published (Hendy, supra) start-stop (ATGTGAAG) signal (deletion is underlined) preceding the used start codon (ATG) to a double start signal (ATGATG).

EXAMPLE 5

Construction of the yeast shuttle vector pL4

Before the HPTH-yeast-expression project was initiated, a family of general yeast expression vectors were developed. One of these, pL4, later was used to make pSS LX5-HPTH1, as described below:

The plasmid pJDB207, constructed by Beggs, J. D., "Multiple-copy yeast plasmid vectors," Von Wettstein, D., Friis, J., Kielland-Brandt, M. and Stenderup, A. (Eds) *Molecular Genetics in Yeast* (1981), Alfred Benzon Symposium Vol. 16, 383–390, was chosen as the basis for the general expression vectors. It contains an EcoRI fragment of the yeast 2 micron DNA inserted into the pBR322 derivative pAT153. It also contains the yeast LEU2 gene. The copy number of pJDB207 in yeast cir+ cells is very high relative to that of other plasmids and it is unusually stable after non-selective growth in a cir+ strain, Parent, S. A., Fenimore, C. M., and Bostian, K. A. "Vector Systems for the Expression, Analysis and Cloning of DNA Sequences in S. cerevisiae". 1 Yeast 83–138 (1985); Erhart, E. and Hollenberg, C. P., "The Presence of a Defective LEV2 Gene on 2 Micron DNA Recombinant Plasmids of *Saccharomyces cerevisiae* is Responsible for Curing and High Copy Number," 156 *J. Bacteriol.* 625–635 (1983). These properties are related to a partial defective promoter in the selective marker gene LEU2 (often named LEU2d, d for defective), Erhart et al., supra, which is not changed in the following constructs.

A 1260 base pair EcoRI-AvaII fragment containing the ADHI promoter was isolated from the plasmid pADH040. After a fill in reaction with the Klenow fragment of DNA polymerase I and all four dNTPs, BamHI linkers were attached and the fragment was cloned into the unique BamHI site of pJDB207. From the plasmid with the promoter in a counterclockwise direction, a 1050 base pair SphI fragment was then deleted (from the SphI site in pJDB207 to the SphI site in the promoter fragment) leaving only a single BamHI site. This plasmid was designated pALX1.

Then the PstI site in the B-lactamase gene of pALX1 was eliminated without inactivating the gene. pALX1 was digested to completion with PstI and nuclease S1 to destroy the PstI site, and then subjected to a partial digestion with PvuI BglI. At the same time a 250 base pair PVUI BglI fragment was isolated from pUCS, Vierira, J. and Messing, J. 19 *Gene* 259 (1982), that contains the corresponding part of a B-lactamase without a PstI site. This was ligated to the partially digested pALX1. In all the ampicillin resistant clones isolated the B-lactamase gene had been restored by incorporating the pUC8 fragment. This plasmid was called pALX2.

The following oligonucleotide was purchased from Prof. K. Kleppe, University of Bergen, and inserted into the BamHI site of pALX2:

```
          BglII       *      *  *   HindIII
      GATCAGATCTGCAGGATGGATCCAAAGCTT              : initiation codon
          TCTAGACGTCCTACCTAGGTTTCGAACTAG    *     : optimal ATG context
              PstI        BamHI
```

Plasmids with the proper orientation were isolated and designated pALX3.

Finally the pALX3 was digested with HindIII and religated to delete a HindIII fragment of 480 base pairs. The resulting vector is called pALX4.

pL4 is a derivative of pALX4 in which the ADHI promoter is deleted. pL4 was used as a basis for the insertion of other promoters. pALX4 was first digested with BglII and SalI. The resulting sticky ends were filled-in with the Klenow fragment of DNA polymerase I and 4 dNTPs followed by religation. By this treatment the ADHI promoter is eliminated and the BglII site regenerated to give the vector pL4.

EXAMPLE 6

Construction of p LX5

The gene for the yeast mating pheromone MF 1 was first cloned by Kurjan, J. and Herskowitz, I., "Structure of a Yeast Pheromone Gene (MF): A Putative -factor Precursor Contains Four Tandem Copies of Mature -factor". 30 *Cell*, 933–943 (1982). The published sequence was used to reclone the MF 1 gene. Total yeast DNA from the strain Y288C was digested with EcoRI and digestion products in the size range from 1.6 to 1.8 kb were isolated from a preparative agarose gel. These were then ligated to dephophorylated EcoRI cleaved pBR322 and used to transform *E. coli* BJ5183. The resulting clones were screened for MF 1 gene inserts by hybridization to a labeled oligonucleotide of the following composition:

TGGCATTGGCTGCAACTAAAGC

DNA from purified positive clones was then used to transform *E. coli* JA221 from which plasmid DNA was prepared. The plasmid used in the following constructs, was pMF 1-1.

pMFα1-1 was digested with EcoRI, filled-in with the Klenow fragment of DNA polymerase I and 4 dNTPs, phenol extracted and digested with BglII. The 1.7 kb MF 1 gene fragment was isolated from an agarose gel. Before inserting it into the yeast shuttle vector, the HindIII site of pL4 was eliminated by HindIII digestion, Klenow fill-in reaction and religation to give the pL5 shuttle vector. pL5 was digested with BamHI, filled-in with the Klenow fragment of DNA polymerase I and 4 dNTPs, phenol extracted and digested with BglII. After purification on gel it was ligated to the MF 1 fragment to give the expression vector pαLX5.

EXAMPLE 7

Construction of pSSαLX5-HPTH1

A 288 base pair BglII XbaI fragment from the pSSHPTH-10 plasmid was isolated and subcloned in pUC19 using the BamHI and XbaI site of this vector. This subclone designated pUC-HPTH, was digested with DpnI and the largest fragment isolated. This fragment was then digested with SalI and the smallest of the two resulting fragments was again isolated, yielding a sticky end on the SalI cut side and a blunt end at the DpnI cut side.

pαLX5 was digested with HindIII, filled-in with the Klenow fragment of DNA polymerase I and 4 dNTPs, phenol extracted and digested with SalI. After purification from gel, it was ligated to the hPTH fragment described above. The resulting clones had the HindIII site regenerated verifying that the reading frame was correct. This plasmid called pSSαLX5-hPTH1 is shown in FIG. 9. The sequence of the MFα1-hPTH fusion gene is shown in FIG. 6.

EXAMPLE 8

Expression And Secretion Of HPTH In Yeast

The yeast strain FL200 (α, ura3, leu2) was transformed with the plasmids pαLX5 and pSSαLX5-HPTH1 using the spheroplast method. One transformant of each kind was grown up in leu⁻ medium and aliquots of the cell-free medium were analyzed by SDS-PAGE developed by silver-staining Two major bands were seen in the medium from the pSSαLX5-H1 transformant that were not present in the medium from the pαLX5 transformant: one band of approximately 9000 daltons, the expected size of HPTH, and one band of approximately 16000 daltons that could correspond to an unprocessed MFα1-HPTH fusion product. Both polypeptides reacted with antibodies against human PTH in a manner identical to the native hormone.

The examples are included by way of illustration, but the invention is not limited thereto. While the above examples are directed to providing a *S. cerevisiae* which produces and excretes human parathyroid hormone, the method of the present invention may be applied to produce a plasmid containing DNA coding for parathyroid hormone from any species. Further, said plasmid may be inserted into any species of yeast. The invention thus is not limited to *S. cerevisiae*.

The cloned human parathyroid hormone produced by the yeast of the present invention has a variety of known and potential uses. For example, it is current medical theory that human parathyroid hormone will be highly effective in treating osteoporosis. Genetically engineered parathyroid hormone may be useful in an analytical kit for measuring parathyroid hormone levels in humans and animals. Human parathyroid hormone or fragments thereof may also be used for treatment of humans or animals displaying reduced or pathologically altered blood calcium levels. It is anticipated that many other uses will be discovered when genetically engineered parathyroid hormone is available in large quantities, for example as a result of the present invention.

EXAMPLE 9

Deletion of the STE 13 recognition sequence positioned N-terminal for the parathyroid hormone In order to delete the STE13 recognition sequence (Glu-Ala-Glu-Ala) located immediately N-terminal to PTH by site directed in vitro mutagenesis of the fusion gene, a 1495 bp XbaI fragment was isolated from pSSαLX5-PTH. This contained the α-factor promoter (MFαprom), the α-factor leader sequence (PP) and the human PTH gene (hPTH) including the stop codon. The fragment was subcloned into M13 mp19 to give the plasmid pαPTHx-M13. An oligonucleotide with the sequence GGATAAAAGATCTGTGAG was made where the first ten nucleotides are complementary to the sequence of the α-factor leader in pαPTHx-M13 just proceeding the Glu-Ala-Glu-Ala coding region, and the last eight nucleotides are complementary to the beginning of the human PTH sequence. When this oligonucleotide was annealed to single-stranded DNA prepared from the recombinant phage, the following heteroduplex was generated:

```
oligonucleotide:   5'-GGATAAAAGATCTGTGAG-3'
p PTHx-M13         3'-CCTATTTTCTAGACACTC-5'
                              C     A
                              T     G  [to be removed]
                           CCGACTTC
translation product .. AspLysArgSerVal ..              (upper)
                  .. AspLysArgGluAlaGluAlaSerVal ... (lower)
```

After second strand synthesis and ligation with the Klenow fragment of DNA polymerase I and T4 DNA ligase, closed circular heteroduplex DNA was isolated by sedimentation through an alkaline sucrose gradient as described in Carter, P., Bedouelle, H., Waye, M. M. Y., and Winter, G. (1985) "oligonucleotide site-directed mutagenesis in M13. An experimental manual," MRC Laboratory of Molecular Biology, Cambridge CB2 2QH., the disclosure of which is hereby incorporated by reference. The heteroduplex DNA was used to transform a BMH 71-18 mutL strain of E. coli defective in mismatch repair (kindly provided by Dr. G. Winter). Positive clones with the looped out sequence 3'-CTCCGACTTCGA-5' deleted were identified by colony hybridization using the mutagenizing oligonucleotide as the probe and by DNA sequencing. The plasmid in these clones was designated paPTHx-M13 EA.

The α-factor transcription terminator was then inserted into one of the positive M13 clones as a SalI HindIII fragment isolated from pMFα1, to give a plasmid called paPTH-M13-ΔEA. The entire expression cassette between a BamHI and a filled-in EcoRI site was finally isolated from paPTH-M13-ΔEA and inserted between the BamHI and PvuII site of the yeast shuttle vector YEp24 by the method described in Botstein, D., Falco, S. C., Stewart, S. E., Brennan, M., Scherer, S., Stinchcomb, D. T., Struhl, K., and Davis, R. W. (1979) *Gene* 8, 17–24, which is hereby incorporated by reference. This expression plasmid was designated pSSαUXPTH-ΔEA.

EXAMPLE 10

Conversion of intact hPTH by substitution of lysine with alitamine at position 26, designated PTH$_{Q26}$, In order to change the amino acid at position 26 in the human PTH from lysine to glutamine, the fusion gene in paPTH-M13-ΔEA was further modified by in vitro mutagenesis using the "Muta-gene ™ in vitro mutagenesis kit" obtained from Bio-Rad based on the method of Kunkel; Kunkel, T. A., Roberts, J. D., and Sakour, R. A. (1987) "Rapid and efficient site-specific mutagenesis without phenotypic selection" in *Methods of Enzyology*, (Wu, R., and Grossman, L., eds.) vol. 154, pp 367–381, which is hereby incorporated by reference. The E. coli strain or CJ236 (dut, ung, thi, rel A; pCJ105 (Cm$^r$)) was transformed with the paPTH-M13-ΔEA plasmid. The single-stranded DNA that was prepared from the phage contained a number of uracils in thymine positions as a result of the dut mutation (inactivates dUTPase) and the ung mutation (inactivates the repair enzyme uracil N-glycosylase). An oligonucleotide with the sequence GGCTGCGTCAGAAGCTGC was made where all nucleotides except the ninth are complementary to an internal PTH sequence in paPTHx-M13. When this oligonucleotide was annealed to the single-stranded DNA, the following heteroduplex was generated:

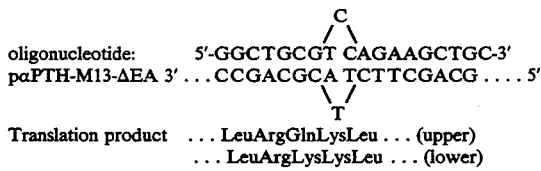

Translation product ... LeuArgGlnLysLeu ... (upper)
... LeuArgLysLysLeu ... (lower)

After second strand synthesis and ligation with T4 DNA polymerase and T4 DNA ligase, the heteroduplex DNA was transformed into the E. coli strain MV1190 ((lac-pro AB), thi, sup E, Δ(srl-rec A) 306::Tn10(tet$^r$)[F,: tra D36, pro AB, lac I$^q$ Z M15]) which contains a proficient uracil N-glycosylase. During the repair process in this host eliminating the uracils in the paternal strand, the in vitro synthesized strand will serve as a repair template conserving the mutation. Positive clones were verified by DNA sequencing. One of those was picked and called paPTH-M13-ΔEA/KQ. The entire expression cassette between a BamHI and a filled-in EcoRI site was finally isolated from paPTH-M13-ΔEA/KQ and inserted between the BamHI and PvuII site of the yeast shuttle vector YEp24. This expression plasmid was designated pSSαUXPTH-ΔEA/KQ.

EXAMPLE 11

Expression and secretion of hPTH$_{Q26}$ in yeast.

The yeast strain BJ1991 (α,Leu2,wa3-52,trp1,pr67-112,pep4-3) was transformed with the plasmids pSSαUXPTH-ΔEA and pSSαUXPTH-ΔEA/KQ using the lithium method. One transformant of each kind was grown in medium lacking uracil and the cell free medium was analyzed as described below.

EXAMPLE 12

Purification Of heterologous hPTH from yeast medium concentration and purification by S-Sepharose $^R$ fast flow Samples of cell free yeast medium (1–10 l) (containing 1% Glucose, 2% casamino acid, 134% yeast nitrogen base w/o amino acids, 60 mg/ml trp, 180 kg/l) were adjusted to pH 3.0 and run through a 10ml×10 S-Sepharose$^R$ (Pharmacia AB) fast flow column, pre-equilibrated with 0.1M glycine pH 3.0. The loaded column was eluted by 13 ml 0.1M acetic acid buffered to pH 6.0, followed by 20 ml 0.1M NH$_4$HC)$_3$ pH 8.5. The peptides eluted from the column were monitored by a Pharmacia optical unit (Single path monitor UVI, Pharmacia AB, Uppsala, Sweden) at 280 nm, and collected in 2 ml fractions by an LKB 2070 Ultrorac II fraction collector (LKB, AB, Bromma, Sweden).

EXAMPLE 13

Purification by HPLC

Collected fractions from S-Sepharose$^R$ fast flow chromatography were subjected to further purification by reversed phase HPLC using a 25 cm×4.2 cm Vydac protein peptide C18 column (The Separations Group, Hesperia, Calif., USA) and an LDC gradient mixer, LDC contamertric pumps model I and III with a high pressure mixing chamber and LDC spectromonitor III with variable UV monitor. (LDC Riviera Beach Fla., USA). Chromatograms were recorded by a Vitatron 2 channel recorder. The analytical conditions were as follows:

First HPLC purification step:
  Gradient: 35–60%B, 60 min., linear
    A: 0.1% trifluoroacetic acid (TFA)
    B: 70% acetonitril in A (ACN)
  Flow: 1.0 ml/min
  Detection: UV 220 nm
Second HPLC purification step:
  Same as first step, with the following modification:
    Gradient: 40–45%B 60 min; linear.

EXAMPLE 14

Assessment of the HPTH$_{Q26}$ product

This PTH analog was verified to represent the designed product by N-terminal amino acid sequence analysis including amino acid no. 30 and shown to be hPTH identical except for the lysine to glutamine substitution at position 26.

Moreover, the resulting amino acid composition had the expected alterations, in that the sequence contained one residue less of lysine and one residue more of glutamine.

Its biological activity was assessed after purification by testing the effect of synthetically bought human parathyroid hormone fitures in comparison to the recombinant analogue which was equally potent in stimulating the adenylyl cyclase of bone cell membranes from rat calveria as well as from an osteosarcoma cell line.

EXAMPLE 15

Additional examples of amino acid substitutions by site specific in vitro mutagenesis By the above method, it is possible to obtain any amino acid substitution or sequences of amino acid alterations in the PTH molecule. By use of the "Muta-Gene ™ in vitro mutagenesis kit" and synthetic oligonucleotides with the desired sequence corresponding to the amino acid alteration(s), this may be carried out. Each of these oligonucleotides can be annealed to the single-stranded DNA in order to generate a hetroduplex as indicated above.

Followed by second strand synthesis and ligation with T4 DNA polymerase and T4 DNA ligase, the heteroduplex DNA is transformed into the E. coli strain MV 1190 with specifications as stated above. In each of these cases, the repair process in this bacterial host will eliminate the uracils in the parenteral strands and at the same time, the in vitro synthesized strand will serve as a repair template whereby the introduced DNA changes will be conserved. All the positive clones will be DNA sequenced and the expression cassettes isolated as described above and inserted into the yeast shuttle vector YEp 24 for transformation of Saccharomyces cerevisiae.

This general approach with the specific alterations as indicated, enables the generation of any desired PTH peptide and PTH like peptide. For example, amino acid substitutions, deletions, insertions or extensions confined within the first 26 amino acids in the N-terminal region can produce agonists with increased affinity for the PTH receptors as well as antagonists which bind to the receptor, but are biologically inactive. The midregion or the C-terminal part of the molecule is of importance for modifying the binding of PTH to the different receptors in bone cells and the kidney. Changes in either of these regions produce an increased or diminished binding affinity to the receptors in bone cells and the kidney, and this may propose specialization in binding characteristics so that the PTH derivative could bind and function only in bone cells or in the kidney, or alteration, i.e., stimulation or blockade, of the biological activity at one or both receptor sites.

The inventions have been described herein with reference to certain preferred embodiments. However, as obvious variations thereon will become apparent to those skilled in the art, the inventions are not to be considered limited thereto.

EXAMPLE 16

Comparison of the Biological Activity of Human Parathyroid Hormone (hPTH 1-84, Bachem Fine Chemicals, Cal. USA) with QPTH The purpose of this study was to compare the biological activity of the recombinant QPTH with the standard PTH preparation of Bachem human PTH (1-84). We examined the ability of the two agents to induce hypercalcemia in rats. Both the maximum plasma calcium levels as well as the duration of action was monitored.

Methods

Male Wistar rats (150–200) were parathyroidectomized using electrocautery 18 hours before the start of the experiment. The animals were fasted overnight, and anesthetized the next day using hypnorm dormicum (0.2 ml per rat). The carotid artery was cannulated using polyethylene-50 tubing. The cannula was connected to a syringe containing Ringers Acetate, 4% bovine serum albumin (BSA), and 25 units heparin/ml. Five minutes after injection of 200 μl of the heparinized Ringers, a baseline blood sample was drawn (300 μl). The animals were trachesostomized to prevent respiratory failure due to damage to the recurrent laryngeal nerve running through the thyroid gland. The PTH was then injected subcutaneously, in a volume of 200 μ. Both hPTH and QPTH had been dissolved into 50 μl of 0.01 N acetic acid, allowing at least one half hour for complete dissolution. After dissolving in the acetic acid, the agents were brought up in 450 μl of Ringers Acetate containing 1% BSA. Blood samples were then drawn at 1, 2, 3, and 4 hours after the injection of the PTH. The rats were reheparinized 5 minutes before drawing each blood sample using 200 μl of the heparinized Ringers solution.

The blood samples were centrifuged in a clinical centrifuge for 10 minutes, then the plasma was analyzed for calcium using a Cobas autoanalyzer.

Both the Bachem hPTH and the QPTH induced hypercalcemia in the rats to about the same degree and lasting about 2 hours. No significant difference in the calcium response was seen until 4 hours after the injections. Then the QPTH maintained the serum calcium better (p<0.05) than synthetic Bachem PTH.

The zero time plasma calcium (baseline) indicates the time of PTH injection and was set equal to zero. The changes in plasma calcium from zero are given as positive or negative values depending on the change (increase or reduction) in the measured values.

| | Time after injection (hrs) [calcium mg/100 ml from baseline] | | | |
|---|---|---|---|---|
| | Median values | | | |
| Preparation | 1 | 2 | 3 | 4 hours |
| Bachem hPTH baseline: 6.84 ± 0.30 (mg/100 ml) | +0.45 | +0.30 | −0.20 | −0.70* |
| QPTH baseline: 7.011 ± 0.29 (mg/100 ml) (n = 7) | +0.55 | +0.25 | 0.0 | −0.50 |

*a significant difference of p 0.05 (Wilcoxon, two-sided test)

REFERENCES

1 Cohn, D. V., and Elting, J. 1983. Biosynthesis, Processing, and Secretion of Parathormone and Secretory Protein-I. In Recent Progress in Hormone Research (Greep, R. O., ed.) vol. 39, pp. 181–209, Academic Press, N.Y.

2 Norman, A. W., Roth, J., and Orci, L. 1982. The vitamin D endocrine system—steroid metabolism, hormone receptors, and biological response (calcium binding proteins). Endocr. Rev. 3, 331–366.

3 Morel, F. 1983. Regulation of Kidney Functions by Hormones: A New Approach. In Greep, R. O. (Ed.), Recent Progress in Hormone Research Academic Press, N.Y., vol. 39, pp. 271-304.

4 Potts, J. T., Kronenberg, H. M., and Rosenblatt, M. 1982. Adv. Protein chem. 32, 323-395.

5 Fiskin, A. M., Cohn, D. V., and Peterson, G. S. 1977. J.Biol.Chem. 252, 8261-8268.

6 Born, W., Freeman, M., Hendy, G. N., Rapoport, A., Rich, A., Potts, J. T. Jr., and Kronenberg, H. M. 1987. Human preproparathyroid hormone synthesized in *Escherichia coli* is transported to the surface of the bacterial inner membrane, but not processed to the mature hormone. Mol. Endocr. 1, 5-14

7 Morelle, G., and Mayer, H. 1988. Biochim. Biophys. Acta 950, 459-462

8 Rabbani, S. A., Yasuda, T., Benett, H. P. J., Sung, W. L., Zahab, D. M., Tam, C. S., Goltzman, D., and Hendy, G. N. 1988. Recombinant Human Parathyroid Hormone Synthesized in *Escherichia coli*. Purification and Characterization. J.Biol.Chem. 263, 1307-1313

9 Gabrielsen, O. S., Reppe, S., Sletten, K., and Oyen, T. B., Sather, O., Hogset, A., Blingsmo, O. R., Gautvik, V. T., Gordeladze, J. O., Alestrom, P., and Gautvik, K. M. 1989. Expression and secretion of human parathyroid hormone in Saccharomyces cerevisiae. Submitted.

10 Bussey, H. 1988. Proteases and the Processing of Precursors to Secreted Proteins in Yeast. Yeast 4, 17-26

11 Fuller, R. S., Sterne, R. E., and Thorner, J. 1988. Enzymes required for yeast prohormone processing Ann. Rev. physiol. 50, 345-362

12 Carter, B. L. A., Irani, M., Mackay, V. L., Seale, R. L., Sledziewski, A. V., and Smith, R. A. 1987. Expression and secretion of foreign genes in yeast. In DNA cloning Volume III. A practical approach. (Glover, D. M., ed.) pp. 141-161, IRL Press, Oxford.

13 Kunkel, T. A., Roberts, J. D., and Zakour, R. A. 1987 Methods in Enzymol,

14 Sanger, F. et al. 1977. Proc. Natl. Acad. Sci. USA 74, 5463

15 Botstein, D., Falco, S. C., Stewart, S. E., Brennan, M., Scherer, S., Stinchcomb, D. T., Struhl, K., and David, R. W. 1979. Sterile host yeast (SHY): a eukaryotic system of biological containment for recombinant DNA experiments. Gene 8, 17-23

16 Gautvik, K. M., Teig, V., Halvorsen, J. F., Arnesen, E., Myhre, L., Heimann, P., and Tollman, R. 1979. Development of sequence specific radioimmunoassay of human parathyroid hormone and its use in the diagnosis of hyperparathyroidism Scand. J. clin. Lab. Invest. 39, 469-478

17 Laemmli, U. K. 1970. Cleavage of structural proteins during assembly of the head of bacteriophage T4. Nature 227, 680-685

18 Bürk, R. R., Eschenbruch, M., Leuthard, P., and Steck, G. 1983. Sensitive Detection of proteins and peptides in polyacrylamide Gels after Formaldehyde Fixation Methods in Enzymol. 91, 247-254

19 Towbin, H., Staehelin, and Gordon, J. 1979. Electrophoretic transfer of proteins from polyacrylamide gels to nitrocellulose sheets: procedure and some applications. Proc. Natl. Acad. Sci. USA 76, 4350-4354

20 Matsudaira, P. 1987. Sequence from picomole Quantities of proteins Electroblotted onto polyvinylidene Difluoride Membranes. J. Biol. Chem. 262, 10035-10038

21 Gautvik, K. M. Gordeladze, J. O., Jahnsen, T., Haug, E., Hansson, V., and Lystad, E. 1983. Gautvik, K. M., Thyroliberin receptor binding and adenylyl cyclase activation in cultured prolactin-producing rat pituitary tumor cells (GH cells). J.Biol.Chem. 258, 10304-10311

22 Gautvik, K. M., Gordeladze, J. O., Moxheim, E., and Gautvik, V. T. 1984. Peripheral Metabolism of Parathyroid Hormone in patients with Primary Hyperparathyroidism as Judged by immunological and Biological Studies. Eur. Surg. Res. 16 (suppl. 2), 41-54

23 Wingender, E., Bercz, G., Blöcker, H., Frank, R., and Mayer, H. 1989. Expression of Human parathyroid Hormone in Escherichia coli. J.Biol.Chem. 264, 4367-4373

24 Niall, H. D., Keutmann, H. T., Sauer, R., Hogan, M., Dawson, B., Aurbach, G. D., and Potts, J. T. Jr. 1974. Hoppe Seylers Z. physiol. Chem. 351, 1586

25 Sauer, R. T., Niall, H. D., Hogan, M. L., Keutmann, H. T., O'Riordan, J. L. H., and Potts, J. T. Jr. 1974. Biochemistry 13, 1994

26 Keutmann, H. T., Sauer, M. M., Hendy, G. N., O'Riordan, J. L. H., and Potts, J. T. Jr. 1978. Complete Amino Acid Sequence of Human parathyroid Hormone. Biochemistry 17, 5723-5729

27 Reeve, J., Meunier, P. J, parsons, J. A., Bernat, M., Bijvoet, O. L. M., Courpron, P., Edouard, C., Klenerman, L., Neer, R. M., Renier, J. C., Slovik, D., Vismans, F. J. F. E., and potts, J. T. Jr. 1980. Anabolic effect of human parathyroid hormone. fragment on trabecular bone in involutional osteoporosis: a multicentre trial. Br.Med.J. 280, 1340-1351

28 Slovik, D. M., Rosenthal, D. I., Doppelt, S. H., Potts, J. T. Jr., Daly, M. A., Campbell, J. A., and Neer, R. M. 1986. Restoration of Spinal Bone in Osteoporotic Men by Treatment With Human parathyroid Hormone (1-34) and 1,25-Dihydroxyvitamin D. J. Bone Min. Res. 1, 377-381

We claim:

1. An isolated intact, functional human parathyroid hormone that is resistant to degradation by a KEX2 like proteolytic enzyme between the amino acids in positions 26 and 27 thereof.

2. The intact, functional human parathyroid hormone of claim 1 wherein Lys in position 26 is substituted with Gln.

3. An intact human parathyroid hormone operably linked to a modified Saccharomyces mating factor alpha 1 wherein a tetramer Glu-Ala-Glu-Ala, disposed immediately N-terminal to said human parathyroid hormone is omitted.

4. An intact human parathyroid hormone operably linked to the Lys Arg KEX2 cleavage site of the leader sequence of Saccharomyces mating factor alpha 1.

5. An intact human parathyroid hormone operably linked to the first 19 amino acids of Saccharomyces mating factor alpha 1.

6. A DNA sequence encoding Saccharomyces mating factor alpha 1 operably linked to a DNA sequence encoding human parathyroid hormone wherein said DNA sequence stably transforms a yeast cell to express and secrete an intact, functional human parathyroid hormone that is resistant to degradation by a KEX2 like proteolytic enzyme between the amino acids in positions 26 and 27 thereof.

7. The DNA sequence encoding Saccharomyces mating factor alpha 1 operably linked to a DNA sequence encoding human parathyroid hormone wherein said DNA sequence encoding human parathyroid hormone is modified such that the codon encoding Lys in position 26 thereof encodes Gln.

8. A DNA sequence encoding Saccharomyces mating factor alpha 1 operably linked to a DNA sequence encoding human parathyroid hormone wherein said DNA sequence encoding said mating factor alpha 1 is modified by deletion of the codons encoding the tetramer Glu-Ala-Glu-Ala disposed immediately N-terminal to said DNA sequence encoding human parathyroid hormone.

9. A DNA sequence encoding Saccharomyces mating factor alpha 1 and human parathyroid hormone wherein said DNA sequence encoding said human parathyroid hormone is operably linked to a DNA sequence encoding the Lys Arg KEX2 cleavage site of the leader sequence of Saccharomyces mating factor alpha 1.

10. A DNA sequence encoding the first 19 amino acids of Saccharomyces mating factor alpha 1 and human parathyroid hormone wherein the DNA sequence encoding human parathyroid hormone is operably linked to a portion of a DNA sequence encoding the first 19 amino acids of said Saccharomyces mating factor alpha 1 and wherein said DNA sequence encoding the first 19 amino acids of Saccharomyces mating factor alpha 1 and human parathyroid hormone which stably transforms a yeast cell to express and secrete on intact, functional human parathyroid hormone.

* * * * *

UNITED STATES PATENT AND TRADEMARK OFFICE
CERTIFICATE OF CORRECTION

PATENT NO. : 5,420,242

DATED : May 30, 1995

INVENTOR(S) : Gautvik et al.

It is certified that error appears in the above-identified patent and that said Letters Patent is hereby corrected as shown below:

On the Title Page under Inventors insert --Odd S. Gabrielsen of Oslo, Norway--.
Column 1, line 11, "19986," should read --1986,--.
Column 2, line 1, "1988" should read --1984--.
Column 2, line 14, "preset" should read --present--.
Column 3, line 56, "size frantionated" should read --size-fractionated--.
Column 3, lines 63-64, "Sta-phyloccous" should read --Sta-phylococcus--.
Column 4, line 18, "(-30)" should read --(~30)--.
Column 4, line 35, before the ".", insert --(Figure 5A)--.
Column 4, line 35, after the word "peak", insert --(Figure 5A)--.
Column 5, line 20, "shown" should read --shows--.
Column 5, line 35, "ug" should read "µg".
Column 5, line 37, "ug" should read "µg".
Column 5, line 40, "ug" should read "µg".
Column 5, line 41, "ug" should read "µg".
Column 6, line 19, "□" should be --■--.

UNITED STATES PATENT AND TRADEMARK OFFICE
CERTIFICATE OF CORRECTION

PATENT NO. : 5,420,242
DATED : May 30, 1995
INVENTOR(S) : Gautvik et al.

It is certified that error appears in the above-identified patent and that said Letters Patent is hereby corrected as shown below:

Column 6, line 25, "$\Delta$" should be --▲--
Column 6, line 35, after the "." insert --ATCC Designation Numbers 40266, 40267, 20821 and 67223--.
Column 6, lines 65-66, "comle-mentary" should read --compl-ementary--.
Column 8, line 6, "withPvuI" should read -- with PvuI--.
Column 8, line 7, "puc8" should read --PuC8,--.
Column 8, line 31, "p LX5. The" should read --pαLX5, the--.
Column 8, line 42, "e-factor" should read --α-factor--.
Column 9, line 17, "e-factor" should read --α-factor--.
Column 9, line 38, "1" should read --$^1$--.
Column 9, line 41, "2-4" should read --$^{2-4}$--.
Column 9, line 52, "1" should read --$^1$--.
Column 9, line 55, "5" should read --$^5$--.
Column 9, line 59, "5-e,uns/8/" should read --$^{6-8}$--.
Column 9, line 62, "9" should read --$^9$--.

UNITED STATES PATENT AND TRADEMARK OFFICE
CERTIFICATE OF CORRECTION

PATENT NO. : 5,420,242

DATED : May 30, 1995

INVENTOR(S) : Gautvik et al.

It is certified that error appears in the above-identified patent and that said Letters Patent is hereby corrected as shown below:

Column 10, line 4, "10,11" should read --$^{10,11}$--.
Column 10, line 25, "12" should read --$^{12}$--.
Column 10, line 28, "paUXPTH-2" should read --pαUXPTH-2--.
Column 10, line 29, "9" should read --$^{9}$--.
Column 10, line 31, "an a-factor" should read --an α-factor--.
Column 10, line 33, "9)" should read --$^{9}$)--.
Column 10, line 34, "TM" should read --$^{TM}$--.
Column 10, line 35, "13" should read --$^{13}$--.
Column 10, line 40, "14" should read --$^{14}$--.
Column 10, line 44, "15" should read --$^{15}$--.
Column 10, line 45, "paUXPTH-Q26" should read --pαUXPTH-Q26--.
Column 10, line 50, "9,16" should read --$^{9,16}$--.
Column 10, line 52, "9" should read --$^{9}$--.
Column 10, line 53, "17" should read --$^{17}$--.
Column 10, line 56, "19" should read --$^{19}$--.

UNITED STATES PATENT AND TRADEMARK OFFICE
CERTIFICATE OF CORRECTION

PATENT NO. : 5,420,242

DATED : May 30, 1995

INVENTOR(S) : Gautvik et al.

It is certified that error appears in the above-identified patent and that said Letters Patent is hereby corrected as shown below:

Column 10, line 58, "9" should read --$^9$--.
Column 10, line 65, "was" should read --were--.
Column 10, line 68, "20" should read --$^{20}$--.
Column 11, line 8, "9,21,22" should read --$^{19,21,22}$--.
Column 11, line 15, "23" should read --$^{23}$--.
Column 11, line 31, "paUXPTH-Q26" should read --pαUXPTH-Q26--.
Column 11, line 38, "paUXPTH-2" should read --pαUXPTH-2--.
Column 12, line 34, "9" should read --$^9$--.
Column 12, line 37, "9,21,22" should read --$^{9,21,22}$--.
Column 13, line 10, "25" should read --$^{25}$--.
Column 13, line 10, "26" should read --$^{26}$--.
Column 13, line 10, "27" should read --$^{27}$--.
Column 15, line 21, "PTHh" should read --hPTH--.
Column 15, line 23, "PTHh" should read --hPTH--.
Column 15, line 39, "starting" should read --Starting--.

UNITED STATES PATENT AND TRADEMARK OFFICE
CERTIFICATE OF CORRECTION

PATENT NO. : 5,420,242

DATED : May 30, 1995

INVENTOR(S) : Gautvik et al.

Page 5 of 8

It is certified that error appears in the above-identified patent and that said Letters Patent is hereby corrected as shown below:

Column 18, line 38, "pUCS," should --pUC8--.
Column 19, line 67, after the phrase "silver-staining and before the word "Two" insert a --.--.
Column 21, line 26, "alitamine" should read --glutamine--.
Column 21, line 26, "PTH$_{Q26}$," should read --PTH$_{Q26}$--.
Column 21, line 31, "Muta-gene-TM" should read --Muta-gene-$^{TM}$--.
Column 21, line 36, "*Enzyology*," should read --*Enzymology*,--.
Column 21, line 63, "F," should read --F'--.
Column 22, line 20, "Of" should read --of--.
Column 22, line 21, "$^R$" should read --$^®$--.
Column 22, line 40, "$^R$" should read --$^®$--.
Column 23, line 18, " TM" should read --$^{TM}$--.
Column 24, line 18, "200 µ." should read --200 µl.--.
Column 24, line 58, "$\underline{1}$" should read --$\underline{1}$--.
Column 24, line 63, "$\underline{2}$" should read --$\underline{2}$--.

UNITED STATES PATENT AND TRADEMARK OFFICE
CERTIFICATE OF CORRECTION

PATENT NO. : 5,420,242
DATED : May 30, 1995
INVENTOR(S) : Gautvik et al.

It is certified that error appears in the above-identified patent and that said Letters Patent is hereby corrected as shown below:

Column 24, line 67, "3" should read --$^3$--.
Column 25, line 3, "4" should read --$^4$--.
Column 25, line 5, "5" should read --$^5$--.
Column 25, line 7, "6" should read --$^6$--.
Column 25, line 13, "7" should read --$^7$--.
Column 25, line 15, "8" should read --$^8$--.
Column 25, line 21, "9" should read --$^9$--.
Column 25, line 27, "10" should read --$^{10}$--.
Column 25, line 30, "11" should read --$^{11}$--.
Column 25, line 33, "12" should read --$^{12}$--.
Column 25, line 38, "13" should read --$^{13}$--.
Column 25, line 39, "1987Methods" should read --1987. Methods--.
Column 25, line 39, after the word "Enzymol" change "," to --.--.
Column 25, line 40, "14" should read --$^{14}$--.
Column 25, line 42, "15" should read --$^{15}$--.

UNITED STATES PATENT AND TRADEMARK OFFICE
CERTIFICATE OF CORRECTION

PATENT NO. : 5,420,242

DATED : May 30, 1995

INVENTOR(S) : Gautvik et al.

It is certified that error appears in the above-identified patent and that said Letters Patent is hereby corrected as shown below:

Column 25, line 47, "16" should read --$^{16}$--.
Column 25, line 53, "17" should read --$^{17}$--.
Column 25, line 56, "18" should read --$^{18}$--.
Column 25, line 60, "19" should read --$^{19}$--.
Column 25, line 65, "20" should read --$^{20}$--.
Column 25, line 65, "picomole" should read --Picomole--.
Column 25, line 66, "proteins" should read --Proteins--.
Column 25, line 66, "polyvinylidene" should read --Polyvinylidene--.
Column 26, line 1, "21" should read --$^{21}$--.
Column 26, lines 2-3, after "1983." cancel "Gautvik, K.M..".
Column 26, line 7, "22" should read --$^{22}$--.
Column 26, line 12, "23" should read --$^{23}$--.
Column 26, line 13, "parathy-" should read --Parathy---.
Column 26, line 16, "24" should read --$^{24}$--.
Column 26, line 19, "25" should read --$^{25}$--.

UNITED STATES PATENT AND TRADEMARK OFFICE
CERTIFICATE OF CORRECTION

PATENT NO. : 5,420,242
DATED : May 30, 1995
INVENTOR(S) : Gautvik et al.

It is certified that error appears in the above-identified patent and that said Letters Patent is hereby corrected as shown below:

Column 26, line 22, "26" should read --$^{26}$--.
Column 26, line 24, "parathyroid" should read --Parathyroid-- .
Column 26, line 26, "27" should read --$^{27}$--.
Column 26, line 29, "potts," should read --Potts,--.
Column 26, line 30, after the word "hormone" cancel the ".".
Column 26, line 33, "28" should read --$^{28}$--.
Column 26, line 36, "parathy-" should read --Parathy---.
Column 26, line 45, after "26" insert --of wild type human parathyroid hormone--.

Signed and Sealed this

Fourth Day of November, 1997

Attest:

Attesting Officer

BRUCE LEHMAN

Commissioner of Patents and Trademarks